US011988656B2

(12) United States Patent
Morrow et al.

(10) Patent No.: US 11,988,656 B2
(45) Date of Patent: May 21, 2024

(54) REMOTE MONITORING OF WATER DISTRIBUTION SYSTEM

(71) Applicant: AMI Investments, LLC, Coppell, TX (US)

(72) Inventors: Brian Morrow, Carrollton, TX (US); Mike Vore, Oskaloosa, IA (US); Charles Kitowski, Colleyville, TX (US); Daniel Copeland, Bessemer, AL (US); Leon G. McCullough, West Des Moines, IA (US); John Thomas Bohrer, Akron, OH (US)

(73) Assignee: McWane, Inc., Birmingham, AL (US)

( * ) Notice: Subject to any disclaimer, the term of this patent is extended or adjusted under 35 U.S.C. 154(b) by 364 days.

(21) Appl. No.: 17/012,625

(22) Filed: Sep. 4, 2020

(65) Prior Publication Data
US 2020/0400643 A1 Dec. 24, 2020

Related U.S. Application Data

(63) Continuation-in-part of application No. 16/428,585, filed on May 31, 2019, now Pat. No. 11,391,712,
(Continued)

(51) Int. Cl.
G01N 33/18 (2006.01)
G01L 19/08 (2006.01)
(Continued)

(52) U.S. Cl.
CPC ............ G01N 33/18 (2013.01); G01L 19/086 (2013.01); H04W 4/021 (2013.01); H04W 4/14 (2013.01)

(58) Field of Classification Search
CPC ........ G01N 33/18; H04W 4/14; H04W 4/021; G01L 19/08; G01L 19/086
(Continued)

(56) References Cited

U.S. PATENT DOCUMENTS 3,585,973 A 6/1971 Klover
3,719,090 A * 3/1973 Hathaway ............. G01N 15/02
73/865.5
(Continued)

FOREIGN PATENT DOCUMENTS

AU 2011274272 B2 5/2015
CA 2517744 A1 3/2006
(Continued)

OTHER PUBLICATIONS

Canadian Examination Report dated Dec. 2, 2020.
(Continued)

Primary Examiner — Peter J Macchiarolo
Assistant Examiner — Jermaine L Jenkins
(74) Attorney, Agent, or Firm — Maynard Nexsen PC; Brian T. Sattizahn

(57) ABSTRACT

A liquid monitoring system includes a remote measurement device located at a location of the fire hydrant that is in contact with water provided by a water main. The remote measurement device has sensors that measure characteristics of the water and/or acoustic vibrations in the water and a communication interface that transmits measured information to a communication network device that may be located elsewhere on the fire hydrant. The communication network device communicates with a communication network.

20 Claims, 16 Drawing Sheets

Related U.S. Application Data which is a continuation of application No. 15/271,597, filed on Sep. 21, 2016, now Pat. No. 10,317,384.

(60) Provisional application No. 62/895,670, filed on Sep. 4, 2019, provisional application No. 62/221,479, filed on Sep. 21, 2015.

(51) Int. Cl.
*H04W 4/021* (2018.01)
*H04W 4/14* (2009.01)

(58) Field of Classification Search
USPC .......................................................... 73/61.71
See application file for complete search history.

(56) References Cited

U.S. PATENT DOCUMENTS

| | | | |
|---|---|---|---|
| 3,980,097 | A | 9/1976 | Ellis |
| 4,055,844 | A | 10/1977 | Hornbostel |
| 4,177,826 | A | 12/1979 | Luckenbill |
| 4,227,544 | A | 10/1980 | Luckenbill |
| 4,435,974 | A * | 3/1984 | Fuchs ................ G01M 3/2807 73/40.5 A |
| 4,608,857 | A | 9/1986 | Mertens et al. |
| 5,441,074 | A | 8/1995 | Kjaer |
| 6,058,957 | A | 9/2000 | Honigsbaum |
| 6,442,999 | B1 | 9/2002 | Baumoel |
| 6,624,628 | B1 | 9/2003 | Kwun et al. |
| 6,751,560 | B1 | 6/2004 | Tingley et al. |
| 6,782,751 | B2 | 8/2004 | Linares et al. |
| 6,820,635 | B1 | 11/2004 | McKeague |
| 6,848,313 | B2 | 2/2005 | Krieg et al. |
| 6,931,445 | B2 | 8/2005 | Davis |
| 6,935,367 | B2 | 8/2005 | Cook et al. |
| 6,957,157 | B2 | 10/2005 | Lander |
| 7,111,817 | B2 | 9/2006 | Teti et al. |
| 7,171,854 | B2 | 2/2007 | Nagashima et al. |
| 7,228,726 | B2 | 6/2007 | Kates |
| 7,231,331 | B2 | 6/2007 | Davis |
| 7,266,992 | B2 | 9/2007 | Shamout et al. |
| 7,274,996 | B2 | 9/2007 | Lapinski et al. |
| 7,418,354 | B1 | 8/2008 | Greenlee et al. |
| 7,475,596 | B2 * | 1/2009 | Hunaidi ............. G01N 29/4418 73/622 |
| 7,596,458 | B2 | 9/2009 | Lander |
| 7,607,351 | B2 | 10/2009 | Allison et al. |
| 7,665,348 | B2 | 2/2010 | Giles |
| 7,668,670 | B2 | 2/2010 | Lander |
| 7,680,625 | B2 | 3/2010 | Throwbridge et al. |
| 7,711,217 | B2 | 5/2010 | Takahashi et al. |
| 7,740,024 | B2 | 6/2010 | Brodeur et al. |
| 7,746,246 | B2 | 6/2010 | Salser, Jr. |
| 7,810,378 | B2 * | 10/2010 | Hunaidi ................ G01M 3/243 73/49.1 |
| 7,837,063 | B2 | 11/2010 | Stoddard |
| 7,980,317 | B1 | 7/2011 | Preta et al. |
| 7,983,869 | B1 | 7/2011 | Hurley |
| 8,109,131 | B2 | 2/2012 | Winter |
| 8,291,990 | B1 | 10/2012 | Mohr |
| 8,362,919 | B2 | 1/2013 | Cooper et al. |
| 8,401,811 | B1 | 3/2013 | Hurley |
| 8,589,092 | B2 | 11/2013 | Plouffe et al. |
| 8,620,602 | B2 | 12/2013 | Alonso |
| 8,640,728 | B2 | 2/2014 | Sigelakis |
| 8,657,021 | B1 | 2/2014 | Preta et al. |
| 8,701,700 | B2 | 4/2014 | Penner et al. |
| 8,701,709 | B2 | 4/2014 | Athanasiades et al. |
| 8,805,633 | B1 | 8/2014 | Hurley |
| 8,931,505 | B2 | 1/2015 | Hyland et al. |
| 8,942,947 | B1 | 1/2015 | Hurley |
| 8,997,777 | B2 | 4/2015 | Montague |
| 9,021,868 | B2 | 5/2015 | Sakamoto et al. |
| 9,467,754 | B1 | 10/2016 | Sparks |
| 9,506,785 | B2 | 11/2016 | Turk |
| 9,596,293 | B2 | 3/2017 | Hirano |
| 9,670,650 | B2 | 6/2017 | Pinney et al. |
| 9,700,746 | B2 | 7/2017 | Bodemann |
| 9,835,592 | B2 * | 12/2017 | Yusuf ................... G01N 29/032 |
| 9,939,344 | B2 * | 4/2018 | Bracken ................ G01M 3/243 |
| 9,983,092 | B2 * | 5/2018 | Howitt .................... E03B 7/071 |
| 10,072,398 | B2 | 9/2018 | Magill et al. |
| 10,317,384 | B2 | 6/2019 | Morrow et al. |
| 10,415,714 | B1 | 9/2019 | Kennedy |
| 10,879,624 | B2 | 12/2020 | Yoshikawa et al. |
| 10,921,304 | B2 | 2/2021 | Morrow et al. |
| 11,054,057 | B2 | 7/2021 | Dolenti |
| 11,186,971 | B1 | 11/2021 | Allen et al. |
| 11,371,977 | B2 | 6/2022 | Morrow et al. |
| 11,391,712 | B2 | 7/2022 | Morrow et al. |
| 11,460,459 | B2 | 10/2022 | Morrow et al. |
| 2002/0023220 | A1 | 2/2002 | Kaplan |
| 2002/0124533 | A1 | 9/2002 | Schmetzer et al. |
| 2002/0124633 | A1 | 9/2002 | Yang et al. |
| 2002/0144731 | A1 | 10/2002 | Heil |
| 2004/0112431 | A1 | 6/2004 | Burlock et al. |
| 2005/0067015 | A1 | 3/2005 | McKeague |
| 2005/0076965 | A1 | 4/2005 | Buckner et al. |
| 2006/0016479 | A1 | 1/2006 | Gonzales |
| 2007/0120664 | A1 | 5/2007 | Bilbrey |
| 2007/0120884 | A1 | 5/2007 | Lecheheb |
| 2007/0163334 | A1 * | 7/2007 | Boyd ................... G01N 1/2035 73/756 |
| 2007/0256842 | A1 | 11/2007 | Mohr |
| 2008/0052094 | A1 | 2/2008 | Morfopoulos et al. |
| 2008/0189056 | A1 | 8/2008 | Heidl et al. |
| 2008/0245420 | A1 | 10/2008 | Davidson et al. |
| 2008/0281534 | A1 | 11/2008 | Hurley |
| 2008/0289402 | A1 | 11/2008 | Chowdhury |
| 2009/0066524 | A1 | 3/2009 | Yukawa et al. |
| 2009/0157521 | A1 | 6/2009 | Moren et al. |
| 2009/0269140 | A1 | 10/2009 | Hater |
| 2009/0320933 | A1 | 12/2009 | Davidson, Sr. et al. |
| 2010/0006654 | A1 | 1/2010 | Poel |
| 2010/0065287 | A1 * | 3/2010 | Burkhart ................ A62C 35/68 169/17 |
| 2010/0066547 | A1 | 3/2010 | Chowdhury |
| 2010/0126590 | A1 | 5/2010 | Walworth |
| 2010/0126601 | A1 | 5/2010 | Heron |
| 2010/0189887 | A1 | 7/2010 | Nielsen |
| 2010/0295672 | A1 | 11/2010 | Hyland et al. |
| 2010/0307609 | A1 | 12/2010 | Burt et al. |
| 2010/0310385 | A1 | 12/2010 | Denne |
| 2011/0094758 | A1 | 4/2011 | Burkhart |
| 2011/0247416 | A1 | 10/2011 | Cooper et al. |
| 2011/0308638 | A1 | 12/2011 | Hyland et al. |
| 2012/0004866 | A1 | 1/2012 | Plouffe et al. |
| 2012/0007743 | A1 | 1/2012 | Solomon |
| 2012/0007744 | A1 | 1/2012 | Pal et al. |
| 2012/0160329 | A1 | 6/2012 | MacKenzie et al. |
| 2012/0244403 | A1 | 9/2012 | Maskew et al. |
| 2012/0305084 | A1 | 12/2012 | Ball et al. |
| 2013/0048318 | A1 | 2/2013 | Ewers |
| 2013/0054121 | A1 | 2/2013 | Casoni |
| 2013/0138396 | A1 | 5/2013 | Hauffen et al. |
| 2013/0192350 | A1 | 8/2013 | Fleury et al. |
| 2013/0199625 | A1 | 8/2013 | Fleury |
| 2013/0206241 | A1 * | 8/2013 | Fleury, Jr. ................. E03B 9/02 137/291 |
| 2013/0314239 | A1 | 11/2013 | Clark |
| 2014/0131463 | A1 | 5/2014 | McCune et al. |
| 2014/0150554 | A1 | 6/2014 | Rada et al. |
| 2014/0165731 | A1 | 6/2014 | Linford |
| 2014/0224026 | A1 | 8/2014 | Linford et al. |
| 2014/0311587 | A1 | 10/2014 | Ellis |
| 2014/0338464 | A1 | 11/2014 | Ball et al. |
| 2014/0340238 | A1 | 11/2014 | Hyland et al. |
| 2015/0082868 | A1 | 3/2015 | Hyland et al. |
| 2015/0241402 | A1 | 8/2015 | Dooley |
| 2015/0376876 | A1 | 12/2015 | Kennedy |
| 2015/0377020 | A1 * | 12/2015 | Kronenberger ......... E21B 21/065 210/91 |
| 2016/0093193 | A1 | 3/2016 | Silvers et al. |
| 2016/0097746 | A1 | 4/2016 | Traub |

(56) References Cited

U.S. PATENT DOCUMENTS

| | | | |
|---|---|---|---|
| 2016/0101307 A1 | 4/2016 | Montague | |
| 2016/0230373 A1 | 8/2016 | Sliger et al. | |
| 2016/0356755 A1 | 12/2016 | Gifford et al. | |
| 2017/0082592 A1* | 3/2017 | Morrow | G01L 19/086 |
| 2017/0130431 A1* | 5/2017 | Pinney | E03B 9/02 |
| 2017/0216645 A1 | 8/2017 | Silvers et al. | |
| 2017/0234712 A1 | 8/2017 | Ball et al. | |
| 2017/0291141 A1 | 10/2017 | Dunham | |
| 2017/0350544 A1 | 12/2017 | Sutton et al. | |
| 2018/0093117 A1 | 4/2018 | Hyland et al. | |
| 2018/0320828 A1 | 11/2018 | Lander et al. | |
| 2019/0128335 A1 | 5/2019 | Li et al. | |
| 2019/0285604 A1 | 9/2019 | Morrow et al. | |
| 2019/0316983 A1 | 10/2019 | Fleury, Jr. et al. | |
| 2020/0088706 A1 | 3/2020 | Morrow et al. | |
| 2021/0140151 A1 | 5/2021 | Johnson et al. | |
| 2022/0003738 A1 | 1/2022 | Morrow et al. | |
| 2022/0003739 A1 | 1/2022 | Morrow et al. | |
| 2023/0014958 A1 | 1/2023 | Morrow et al. | |
| 2023/0062462 A1 | 3/2023 | Morrow et al. | |

FOREIGN PATENT DOCUMENTS

| | | | |
|---|---|---|---|
| CA | 2592125 A1 | 12/2007 | |
| CA | 2801242 A1 | 1/2012 | |
| CA | 2801242 C | 5/2014 | |
| CA | 3002309 C | 9/2020 | |
| CA | 3149224 A1 | 3/2021 | |
| CN | 202740674 U | 2/2013 | |
| CN | 103244828 A | 8/2013 | |
| CN | 203750085 U | 8/2014 | |
| CN | 104368112 A | 2/2015 | |
| CN | 204781115 U | 11/2015 | |
| CN | 205084293 U | 3/2016 | |
| CN | 205088745 U | 3/2016 | |
| CN | 205978525 U | 2/2017 | |
| CN | 208823861 U | 5/2019 | |
| EP | 2735783 A1 | 5/2014 | |
| JP | 2012011115 A | 1/2012 | |
| KR | 101556590 B1 | 10/2015 | |
| WO | 2012000088 A1 | 1/2012 | |
| WO | 2014189901 A1 | 11/2014 | |
| WO | 2017/053396 A1 | 3/2017 | |
| WO | 2017/175135 A1 | 10/2017 | |
| WO | 2017175136 A1 | 10/2017 | |
| WO | 2021/046340 A1 | 3/2021 | |

OTHER PUBLICATIONS

International Patent Application No. PCT/US2016/052840, "International Preliminary Report on Patentability," dated Apr. 5, 2018.
The International Search Report for PCT/US20/49388 dated Dec. 8, 2020.
International Search Report and Written Opinion mailed on Dec. 8, 2016, in International Patent Application No. PCT/US2016/052840, filed on Sep. 21, 2016, 7 Pages.
Office Action mailed on Apr. 9, 2019, in Canadian Patent Application No. 2,999,489, filed on Sep. 21, 2016, 3 Pages.
Office Action mailed on Feb. 28, 2020, in Canadian Patent Application No. 2,999,489, filed on Sep. 21, 2016, 4 Pages.
International Preliminary Report on Patentability received for International Patent Application No. PCT/US2020/049388, mailed on Mar. 17, 2022, 08 pages.
Office Action received for Canadian Patent Application No. 3149224, mailed on Nov. 17, 2023, 3 Pages.

* cited by examiner

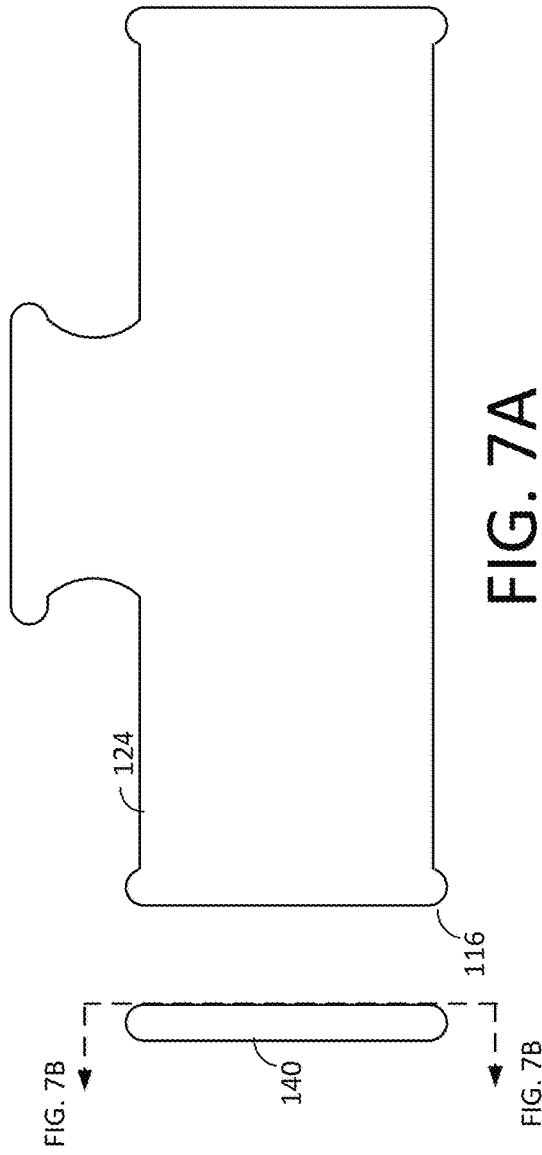
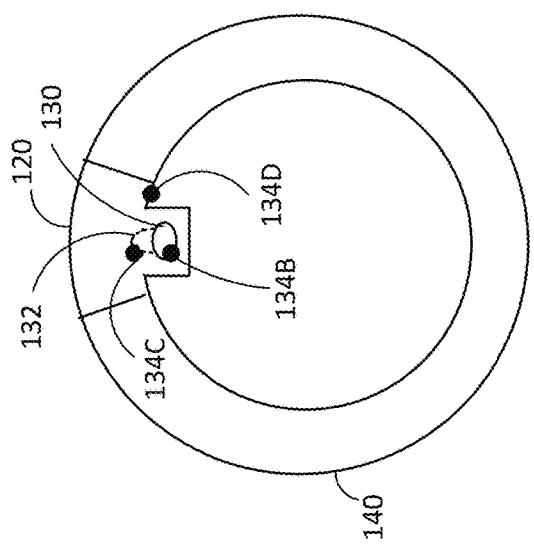
FIG. 7A
FIG. 7B

REMOTE MONITORING OF WATER DISTRIBUTION SYSTEM

CROSS-REFERENCE TO RELATED APPLICATIONS

This application claims the benefit of U.S. Provisional Application No. 62/895,670, entitled "Remote Monitoring of Water Distribution System," filed Sep. 4, 2019 and is a continuation-in-part of U.S. application Ser. No. 16/428,585, entitled "Remote Monitoring of Water Distribution System," filed May 31, 2019, which is a continuation of U.S. application Ser. No. 15/271,597, entitled "Remote Monitoring of Water Distribution System," filed Sep. 21, 2016, which claims the benefit of U.S. Provisional Application No. 62/221,479, entitled "Remote Monitoring of Water Distribution System," filed Sep. 21, 2015, both of which applications are hereby incorporated by reference in their entirety.

BACKGROUND

Water distribution systems provide water to homes and businesses within a geographic area. The water is treated by a water treatment system prior to distribution in order to ensure that it complies with legal, regulatory, and customer requirements relating to the quality and content of the distributed water. For example, some legal or regulatory requirements may relate to the maximum content of certain chemicals or materials within the water. Customer requirements may not be legally enforced but may nonetheless be related to the desirable taste, smell, and appearance of the water that is distributed to customers who are served by the water distribution system.

A water distribution system may cover a large geographic area. Leaks or blockages within the system may result in a reduced level of service provided to customers and loss of valuable water resources. In some cases, undesirable chemicals or materials could be introduced to the water distribution system after the water leaves the treatment facility, at some intermediate locations within the water distribution system. The water mains that distribute water within the water distribution system are located underground, and are therefore difficult to access or monitor.

BRIEF DESCRIPTION OF THE DRAWINGS

The above and other features of the present disclosure, its nature and various advantages will be more apparent upon consideration of the following detailed description, taken in conjunction with the accompanying drawings in which:

FIG. 7A shows an exemplary embodiment of a remote measurement device located within a flange insert in accordance with some embodiments of the present disclosure;

FIG. 7B depicts a perspective view of the flange insert in accordance with some embodiments of the present disclosure;

DETAILED DESCRIPTION

A water distribution system has a water treatment facility that supplies water to an area such as a municipality, industrial park, commercial area, mixed use area or development, and various other locations and environments. The water is distributed through water mains, and fire hydrants are located throughout the water distribution system. These fire hydrants may be either dry-barrel hydrants or wet-barrel hydrants depending on the environment in which the hydrant is to be installed. Whatever the manner of construction, the hydrant includes a main valve that can be opened in order to provide water from the water main to nozzles of the hydrant. The water running thought the water main is pressurized, and in this manner, delivers pressurized water to the fire hydrant.

A typical water distribution system may cover a large geographic area. As a result, even though the water that is provided from the water distribution system may be compliant with legal, regulatory, and customer requirements, it is possible that problems with the water may be introduced elsewhere within the water distribution system as a whole. This may result in pressure losses within the water distribution system or the introduction of undesirable chemicals or materials at remote locations within the water distribution system.

The fire hydrants are located throughout the water distribution system, and may provide a location for remote monitoring of conditions of the water distribution system such as water pressure, water temperature, water quality, chemical content, solid content, or any other suitable characteristics of the water within the water distribution system. A remote measurement device may be located at a location where it is exposed to the water flow of the water distribution system, for example, at the main valve of a fire hydrant or as an insert that connects to a flange of the fire hydrant. The remote measurement device may include sensors that measure any suitable characteristics of the water or the water distribution system, such as pressure, temperature or characteristics of the water.

The remote measurement device may include a processor that processes the output of the sensors, and in some embodiments, calculates measurement values based on the sensor outputs. The remote measurement device may also include a communication interface that transmits the sensor outputs and other calculated values to a communication network device that is located at the fire hydrant, for example, near the bonnet of the fire hydrant (e.g., within a cap of the fire hydrant). This information may be communicated through either a wired connection or wirelessly. The communication network device of the fire hydrant may communicate this information to a monitoring system of the water distribution system. This information may be used by the monitoring system to identify problems within the water distribution system.

Figure 1:
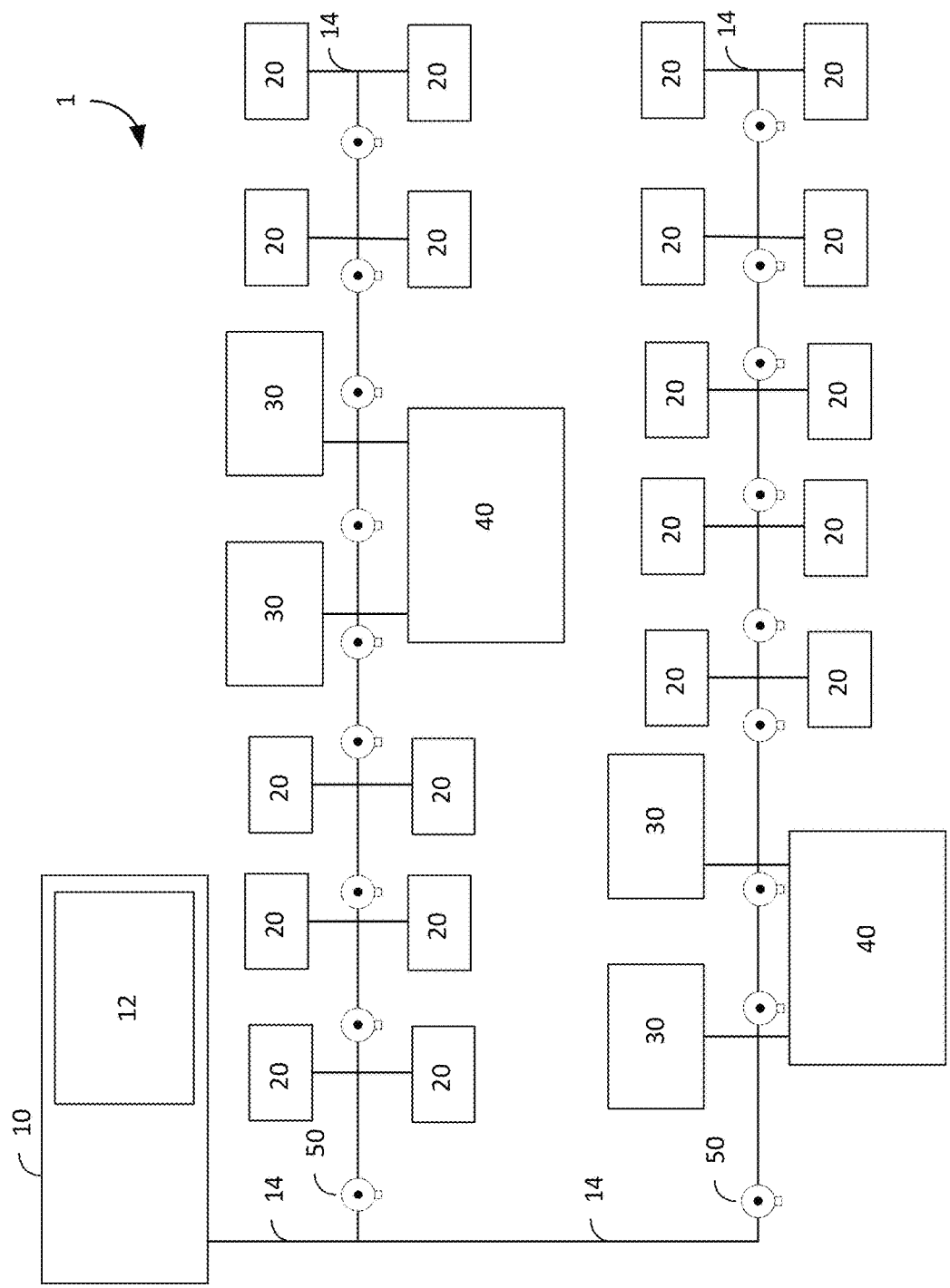
FIG. 1 shows an illustrative water distribution system in accordance with some embodiments of the present disclosure.

FIG. 1 shows an illustrative water distribution system 1 in accordance with some embodiments of the present disclosure. In one embodiment, the water distribution system may include a water treatment facility 10 that includes a central monitoring system 12. Water is provided to the water treatment facility 10 from a water source (not depicted). Water treatment facility 10 treats the water that is provided from the water source such that it complies with legal, regulatory, and customer requirements related to water content and quality. Central monitoring system 12 may receive information from remote measurement devices that are located throughout the water distribution system 1 (e.g., at fire hydrants 50) in order to ensure that water that is delivered to different locations throughout the water distribution system 1 complies with the legal, regulatory, and customer requirements. Based on this information, the central monitoring system 12 may report problems within the water distribution system 1 and suggest corrective action such as needed repairs at a location of the water distribution system 1.

In one embodiment, the central monitoring system 12 may identify locations where there is an unexpected loss of pressure within the water distribution system 1. Based on this information, the location where an inspection or repair needs to be made may be pinpointed accurately. In a similar manner, the central monitoring system 12 may monitor characteristics of the water, such as material or chemical content, at different locations throughout the water distribution system 1. Based on these characteristics, the central monitoring system 12 may identify a location where water quality does not comply with legal, regulatory, or customer requirements. In addition, central monitoring system 12 may monitor aspects of the water distribution system 1 over time, for example, to determine usage patterns or other changes to the water distribution system 1.

The water that is provided by the water treatment facility 10 may be provided to water main(s) 14. The water main(s) 14 may distribute the water to customers such as residential customers 20, business customers 30, and industrial customers 40. In some embodiments (not depicted herein), remote measurement devices may be located at one or more of these customer locations in addition to the fire hydrants 50 or instead of the fire hydrants 50. However, as described in more detail herein, at least some of the remote measurement devices may be located at the fire hydrants 50 of the water distribution system 1. This may provide some advantages, for example, that the party that owns or manages the water distribution system 1 is likely to have access to and at least partial control over the fire hydrants 50 and the operation thereof.

Figure 2:
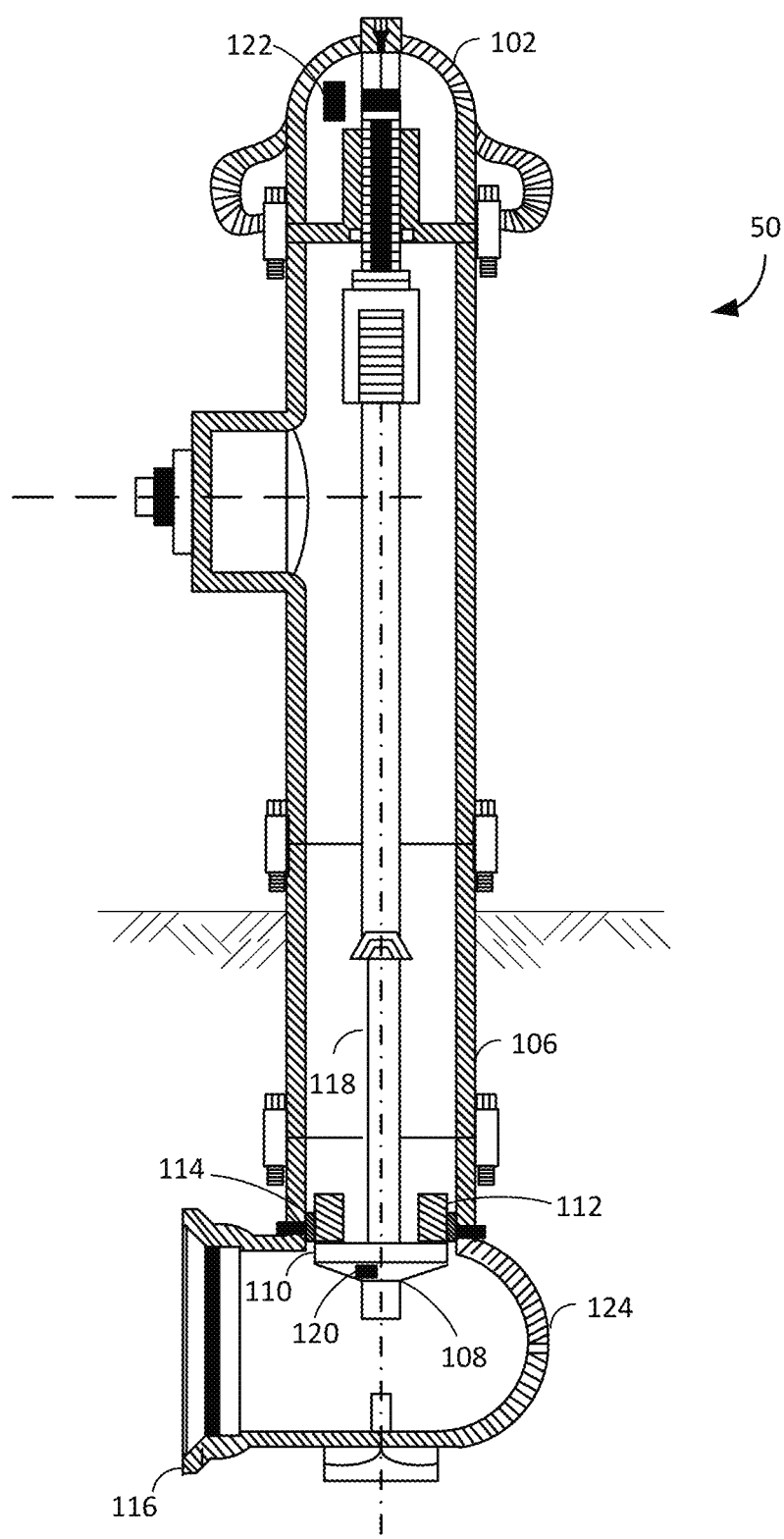
FIG. 2 shows an exemplary fire hydrant including a remote measurement device in accordance with some embodiments of the present disclosure.

FIG. 2 shows an exemplary fire hydrant 50 including a remote measurement device and communication network device in accordance with some embodiments of the present disclosure. Although any suitable type of fire hydrant may be utilized in accordance with the present disclosure (e.g., a dry-barrel or wet-barrel fire hydrant), in one embodiment as depicted in FIG. 2 the fire hydrant 50 may be a dry-barrel fire hydrant. In one embodiment, the fire hydrant 50 may include a remote measurement device 120 and a communication network device 122. Although certain fire hydrant components will be described in accordance with the present disclosure, it will be understood that the remote measurement device 120 and/or communication network device 122 may be implemented at any suitable location within any suitable fire hydrant 50.

In some embodiments, the fire hydrant 50 may include a shoe 124 that connects to a water main 14 (not shown in FIG. 2) via a flange 116. A main valve of the fire hydrant 50 may include a lower valve plate 108 and a valve seat 110. Under normal conditions when water is not being provided to the fire hydrant 50, the lower valve plate 108 may provide a force upon the valve seat 110 such that it creates a seal with seat ring 112 and an upper valve plate (not depicted). A valve stem 118 may be coupled to the lower valve plate 108 such that a user of the fire hydrant may release the seal between the valve seat 110 and the seat ring 112, allowing water from the water main 14 to be provided to the fire hydrant 50 via barrel 106. In some embodiments, seat ring 112 may engage with a drain ring 114, such that the valve stem 118, seat ring 112, and main valve (e.g., including lower valve plate 108 and valve seat 110) may be selectively removed and serviced at the fire hydrant 50. In this manner, a remote measurement device 120 may be accessed and serviced as necessary, for example, to replace a battery of remote measurement device 120.

In one embodiment, a remote measurement device 120 may be located in a location that is suitable to measure characteristics of the water that is distributed through the water main 14 of the water distribution system 1. For example, the water main may be coupled to the shoe 124 via flange 116. Although the remote measurement device 120 may be located in any suitable location that is in contact with the water provided by water main 14 (e.g., at any location of shoe 124), in one embodiment the remote measurement device 120 may be located at an exposed surface of the lower valve plate 108.

Figure 3:
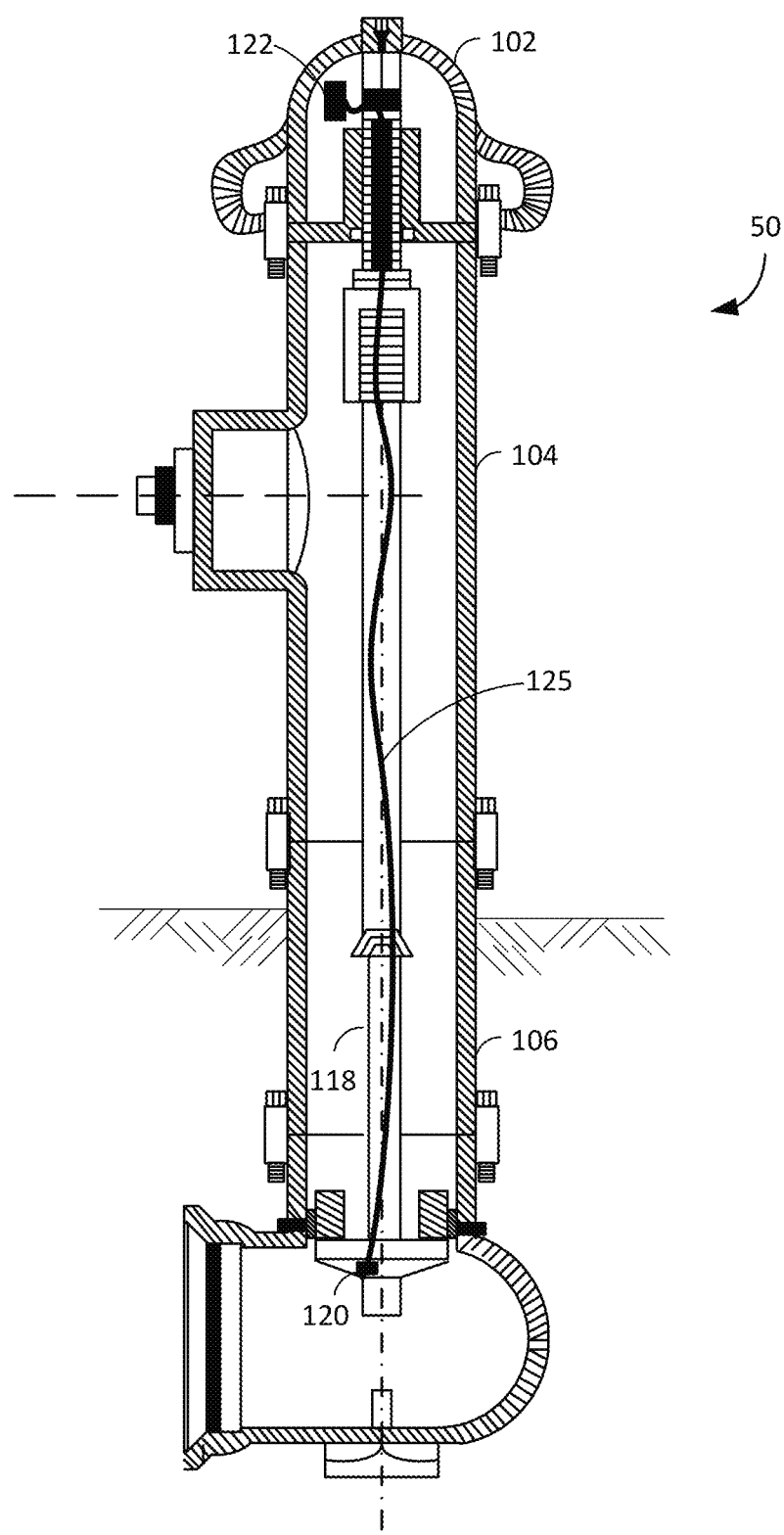
FIG. 3 shows an exemplary fire hydrant including a remote measurement device and valve stem communication path in accordance with some embodiments of the present disclosure.
Figure 4:
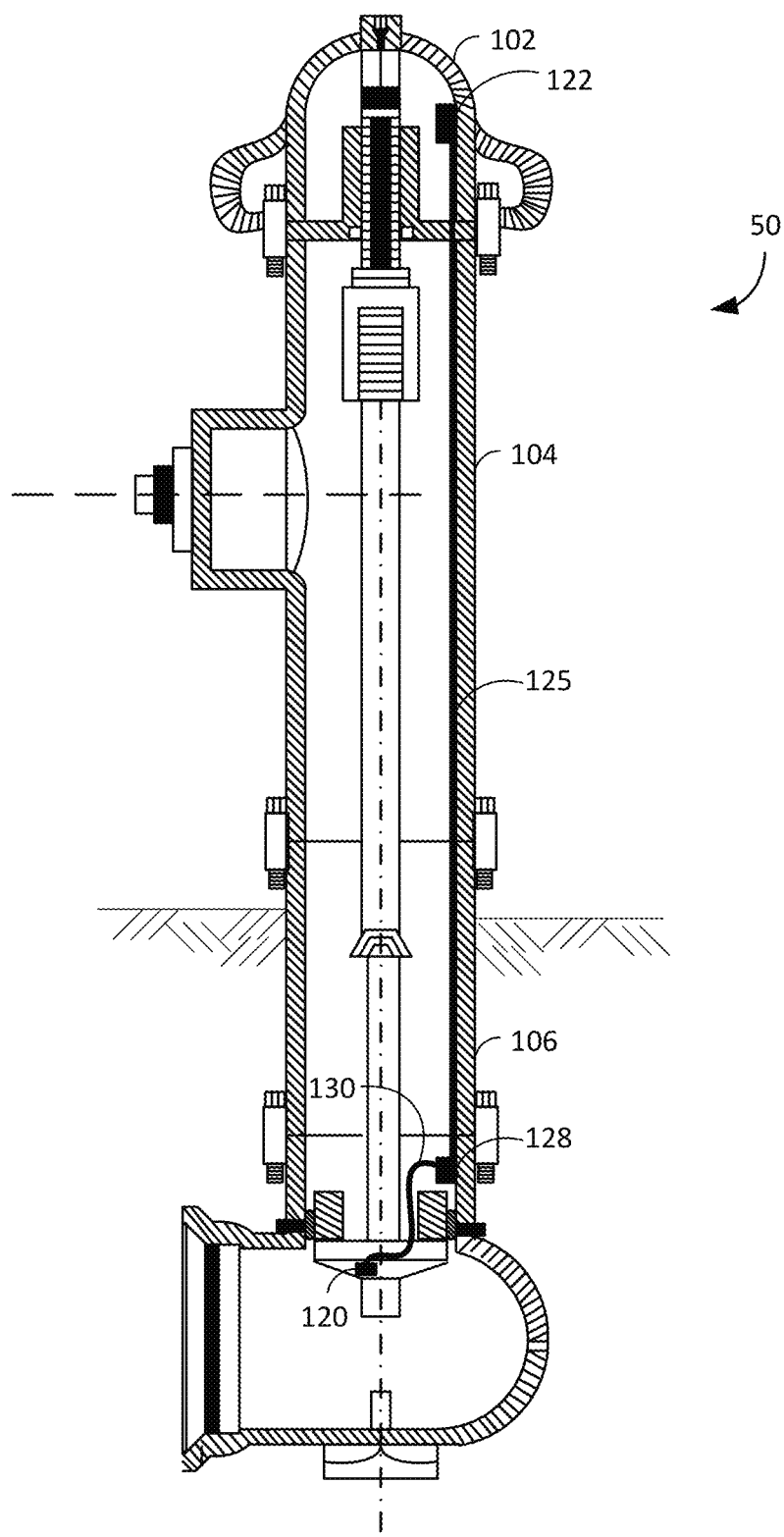
FIG. 4 shows an exemplary fire hydrant including a remote measurement device and barrel communication path in accordance with some embodiments of the present disclosure.

The remote measurement device 120 may include any suitable components to provide for measurement of characteristics of water provided by the water main 14. In one embodiment, the remote measurement device 120 may include a plurality of sensors that measure characteristics of the water such as pressure, temperature, turbidity, heave, material content (e.g., total dissolved solids), biological content, chemical content (e.g., chlorine), or any other suitable characteristics. The measured characteristics may be processed at the remote measurement device 120, or some or all of the outputs of the plurality of sensors may be provided to another device (e.g., communication network device 122) for further processing. In some embodiments, the remote measurement device 120 may communicate with the communication network device 122 via a standardized wireless communication protocol (e.g., WiFi, ZigBee, Bluetooth, Bluetooth low energy, etc.) or proprietary wireless communication protocol operating at frequency such as 900 MHz, 2.4 GHz, or 5.6 GHz. In other embodiments, the remote measurement device 120 may communicate with a communication network device 122 via a wired connection, for example, that is routed through a cavity of valve stem 118 (e.g., as depicted in FIG. 3) or that is positioned along an interior surface of barrel 106 (e.g. as depicted in FIG. 4).

In one embodiment, communication network device 122 may be located at a location of fire hydrant 50 that is located above ground, for example, at a location within bonnet 102 of the fire hydrant 50. However, it will be understood that communication network device 122 may be located at any suitable location of fire hydrant 50, including an interior or exterior surface of fire hydrant 50. In addition, in some embodiments, the communication network device 122 and the remote measurement device 120 may be integrated as a single component (e.g., with the communication network device 122 located with remote measurement device 120 at a location that is in contact with water from water main 14, or in a wet-barrel fire hydrant 50).

Communication network device 122 may be in communication with the remote measurement device 120 and may also be in communication with a communication network and/or central monitoring system 12. In some embodiments, communication network device 122 may also be in communication with other communication devices such as network communication devices 122 of other fire hydrants 50 within the water distribution system 1. As described herein, the communication network device 122 may include a wired or wireless communication interface that is compatible with the remote measurement device 120 as well as one or more additional wireless communication interfaces for communicating with the communication network and central monitoring system 122, such as a cellular communication network or mesh communication network. In an exemplary embodiment of a cellular communication network, the communication network device 122 may communicate in any suitable manner, such as via internet protocol data communication or short message system (SMS) messages. In an exemplary embodiment of a mesh communication system, data may be transmitted to the central monitoring system 12 via the mesh network or using a data collection procedure (e.g., using a service vehicle to survey the communication network devices 122 at hydrants 50).

In one embodiment, not depicted herein, rather than providing some or all of the sensors at a location that is in contact with the water passing through the water main 14, it may be possible to provide water to a remote location relative to the water main, for example, using a pitot tube located at the lower valve plate 108, valve seat 110, or shoe 124. Water may be provided via the pitot tube or other similar device such that one or more sensors may be located above ground, for example, directly to network communication device 122 located at a location of bonnet 102.

FIG. 3 shows an exemplary fire hydrant 50 including a remote measurement device 120 and valve stem 118 communication path in accordance with some embodiments of the present disclosure. As is depicted in FIG. 3, a wired connection 125 may be provided between the remote measurement device 120 and the communication network device 122. In the exemplary embodiment of FIG. 3, the wired connection 125 may be located within an interior cavity of the valve stem 118. Although the wired connection 125 may be provided in any suitable manner, in some embodiments, the wired connection may include some slack such that the wired connection is able to accommodate movement of the main valve and valve stem 118.

Any suitable signals or combination thereof may be provided via wired connection 125, including but not limited to sensor signals from remote measurement device 120, data signals between remote measurement device 120 and communication network device 122, and power signals provided to remote measurement device 120 and communication network device 122. In one embodiment, remote measurement device 120 may receive power via wired connection 125 and may provide analog or digital signals directly from sensors of remote measurement device 120. In another exemplary embodiment, remote measurement device 120 may process some or all of the signals received at sensors thereof and communicate values determined therefrom to communication network device 122 via a data signal. A data signal may be provided by any suitable standardized or proprietary protocol, such as USB, I²C, GPIO, SPI, or Firewire.

FIG. 4 depicts an exemplary fire hydrant 50 including a remote measurement device 122 and barrel 106 communication path in accordance with some embodiments of the present disclosure. As described for FIG. 3, the communication path depicted in FIG. 4 may include a wired connection 125 between remote measurement device 120 and communication network device 122. As depicted in FIG. 4, the wired connection 125 may be routed along an interior surface of barrel 106. The wired connection may be coupled along the interior surface in any suitable manner, for example, via a channel provided within the interior surface of the fire hydrant 50. In one embodiment, a coupling 128 and connecting wire 130 may be provided at a location relative to the main valve (e.g., in an embodiment wherein the remote measurement device 120 is located at the main valve) and may allow for the connecting wire 130 to extend along with movements of the main valve.

Figure 5:
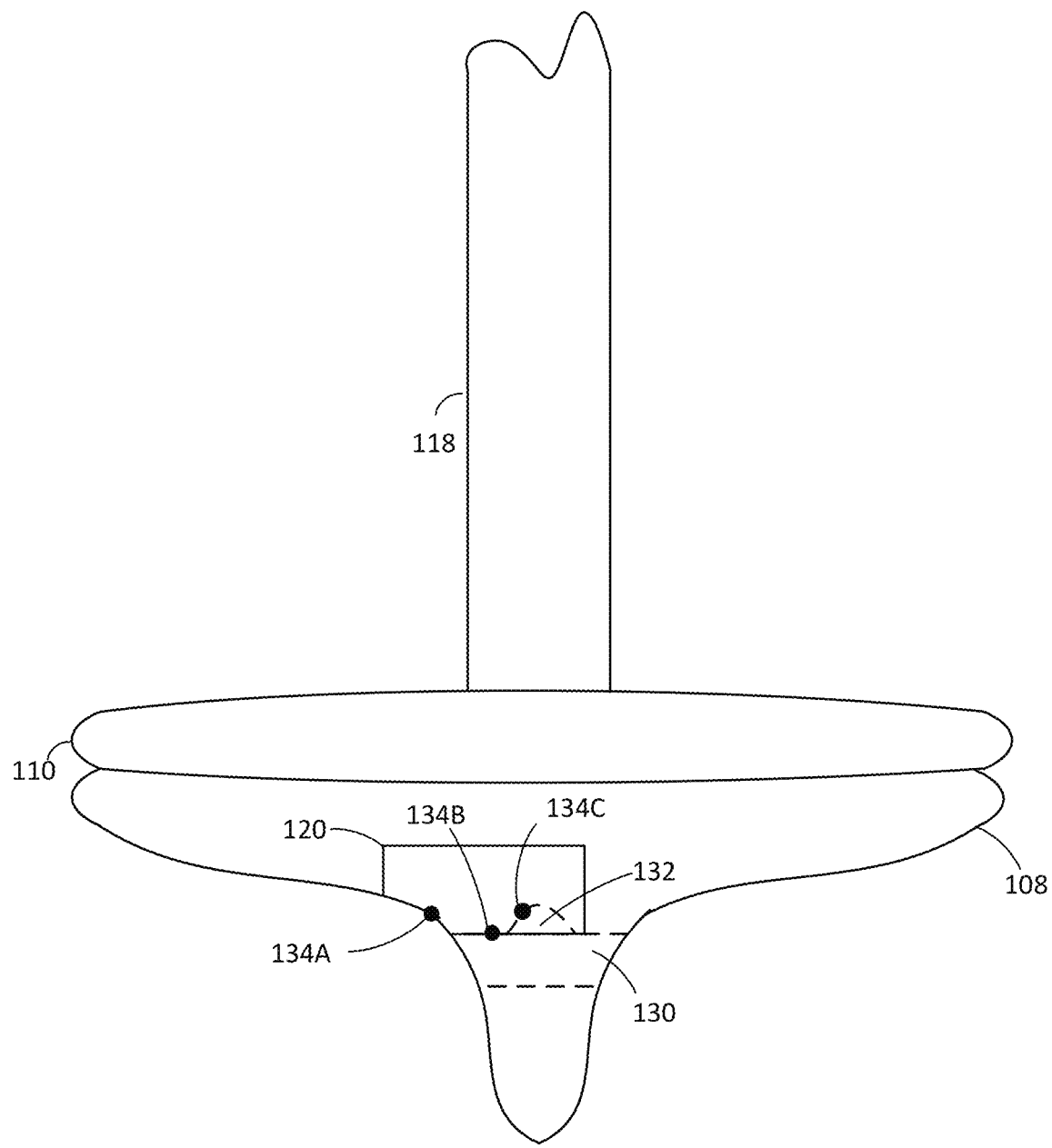
FIG. 5 shows an exemplary remote measurement device located within a cavity of a lower valve plate of a fire hydrant in accordance with some embodiments of the present disclosure.

FIG. 5 shows an exemplary remote measurement device 120 located within a cavity of a lower valve plate 108 of the main valve of a fire hydrant 50 in accordance with some embodiments of the present disclosure. As described herein, a remote measurement device 120 may be integrated into any suitable component of a fire hydrant 50 that is in contact with water supplied by a water main 14. In one embodiment, the remote measurement device 120 may be integral to the lower valve plate 108 (e.g., located within a cavity of the lower valve plate 108). The lower valve plate 108 may have a sealing surface that creates a seal with the valve seat 110 and an exposed surface located opposite the sealing surface.

Remote measurement device 120 may include sensors 134 that may determine characteristics of the water of water main 14. Examples of sensors 134 may include pressure sensors, temperature sensors, turbidity sensors, heave sensors, sensors for material content (e.g., total dissolved solids), sensors for biological content, sensors for chemical content (e.g., chlorine), or sensors for any other suitable characteristics. Sensors 134 may be configured as electrical sensors, mechanical sensors, electromechanical sensors, optical sensors, acoustic sensors, any other suitable type of sensor, or any combination thereof.

In some embodiments, sensors 134 may be provided at a variety of locations of lower valve plate 108 or another similar component. As depicted in FIG. 5, sensor 134A may be provided at an exterior surface of lower valve plate 108. In some embodiments, a channel 130 may be provided through lower valve plate 108. As depicted in FIG. 5, a sensor 134B may be located at the surface of channel 130, or in some embodiments, within channel 130. A reservoir 132 may also be provided within lower valve plate 108, and one or more sensors 134C may be provided within reservoir 132. In some embodiments, the sensors 134B or 134C located at or in the channel 130 or reservoir 132 may include a liquid sampling device that is configured to acquire a sample of the liquid and to determine the one or more characteristics based on the sample.

Figure 6:
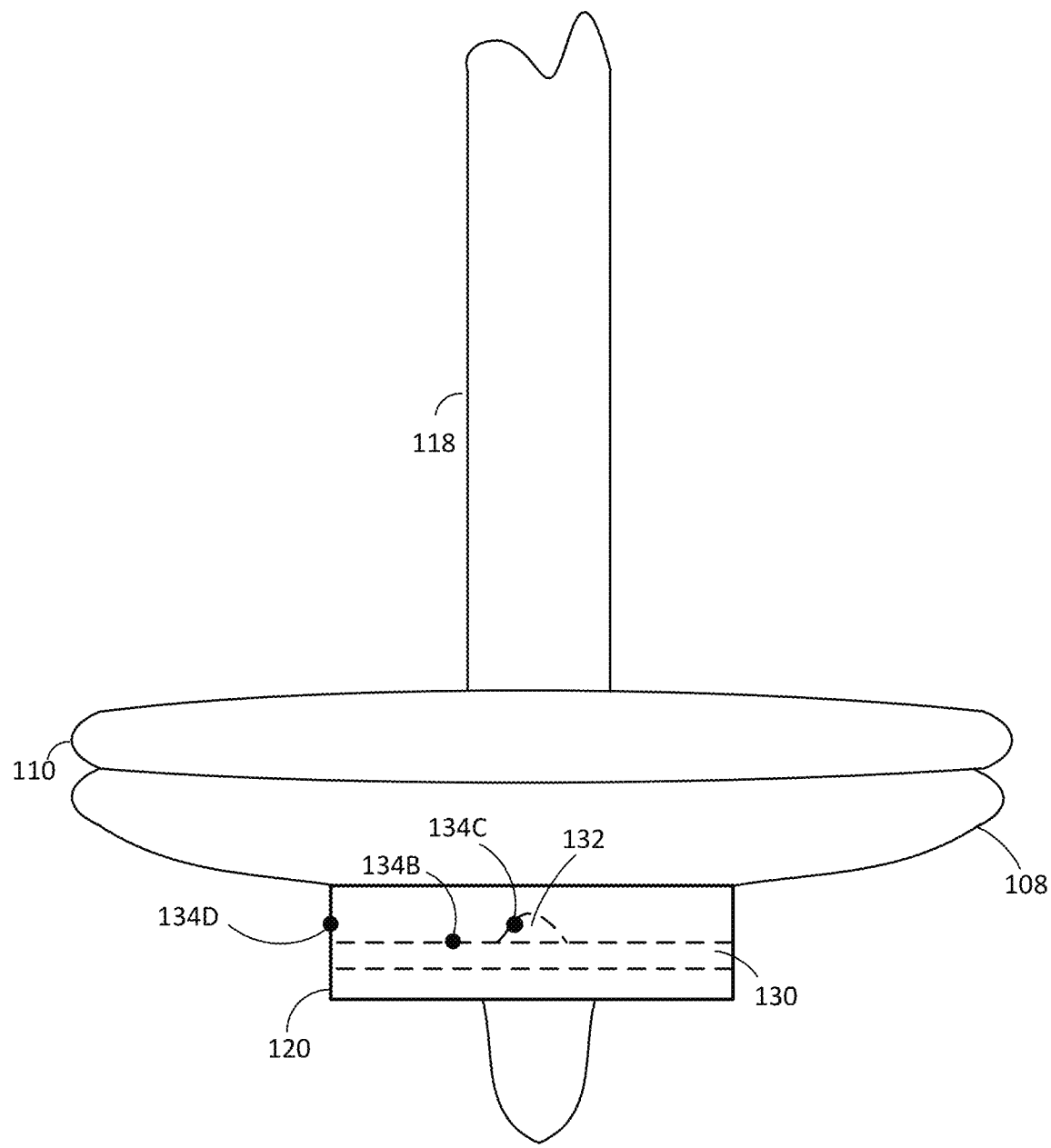
FIG. 6 shows an exemplary remote measurement device located at an exterior surface of a lower valve plate of a fire hydrant in accordance with some embodiments of the present disclosure.

FIG. 6 shows an exemplary remote measurement 120 device located at an exterior surface of a lower valve plate 108 of the main valve of a fire hydrant 50 in accordance with some embodiments of the present disclosure. As described herein, a remote measurement device 120 may be located at an exterior surface of any suitable component of a fire hydrant 50 that is in contact with water supplied by a water main 14. In one embodiment, the remote measurement device 120 may be fixedly attached to the lower valve plate 108 (e.g., via a weld, bolt, or any other suitable attachment mechanism). The lower valve plate 108 may have a sealing surface that creates a seal with the valve seat 110 and an exposed surface located opposite the sealing surface, to which the remote measurement device is attached.

Similar to FIG. 5, remote measurement device 120 may include sensors 134 that may determine characteristics of the water of water main 14. Examples of sensors may include pressure sensors, temperature sensors, turbidity sensors, heave sensors, sensors for material content (e.g., total dissolved solids), sensors for biological content, sensors for chemical content (e.g., chlorine), or sensors for any other suitable characteristics. Sensors 134 may be configured as electrical sensors, mechanical sensors, electromechanical sensors, optical sensors, acoustic sensors, any other suitable type of sensor, or any combination thereof.

In some embodiments, sensors 134 may be provided at a variety of locations of the remote measurement device 120. Sensors 134 may be provided at an exterior surface of remote measurement device 120 (sensor 134D), at or within a channel 130 of remote measurement device 120 (sensor 134B), and/or at or within a reservoir 132 of remote measurement device 120 (sensor 134C).

FIG. 7A shows an exemplary embodiment of a remote measurement device 120 located within a flange insert 140 in accordance with some embodiments of the present disclosure. As described herein, a fire hydrant 50 may include a shoe 124 having a flange 116 that attaches to a water main 14 (not shown). In one embodiment, a flange insert 140 may be provided that includes the remote measurement device 120. The flange insert 140 may be located between flange 116 and the water main 14, and may be fixedly attached to both in any suitable manner (e.g., bolts and nuts (not depicted)). In a similar manner as is described and depicted for the remote measurement device 120 of FIGS. 2-6, a remote measurement device 120 located at a flange insert 140 may communicate with a communication network device 122 via a wired or wireless connection. In the exemplary embodiment of a wired connection 125, the wired connection 125 may be provided at an interior or exterior surface of the fire hydrant 50.

FIG. 7B depicts a perspective view of the flange insert 140 in accordance with some embodiments of the present disclosure. Although a flange insert may be implemented in any suitable manner, in some embodiments the flange insert 140 may include a remote measurement device 120 located within a portion thereof. As described herein for the remote measurement device 120 of FIGS. 5-6 and depicted in FIG. 7B, sensors 134 may be provided at an exterior surface of remote measurement device 120 (sensor 134D), at or within a channel 130 of remote measurement device 120 (sensor 134B), and/or at or within a reservoir 132 of remote measurement device 120 (sensor 134C).

Figure 8:
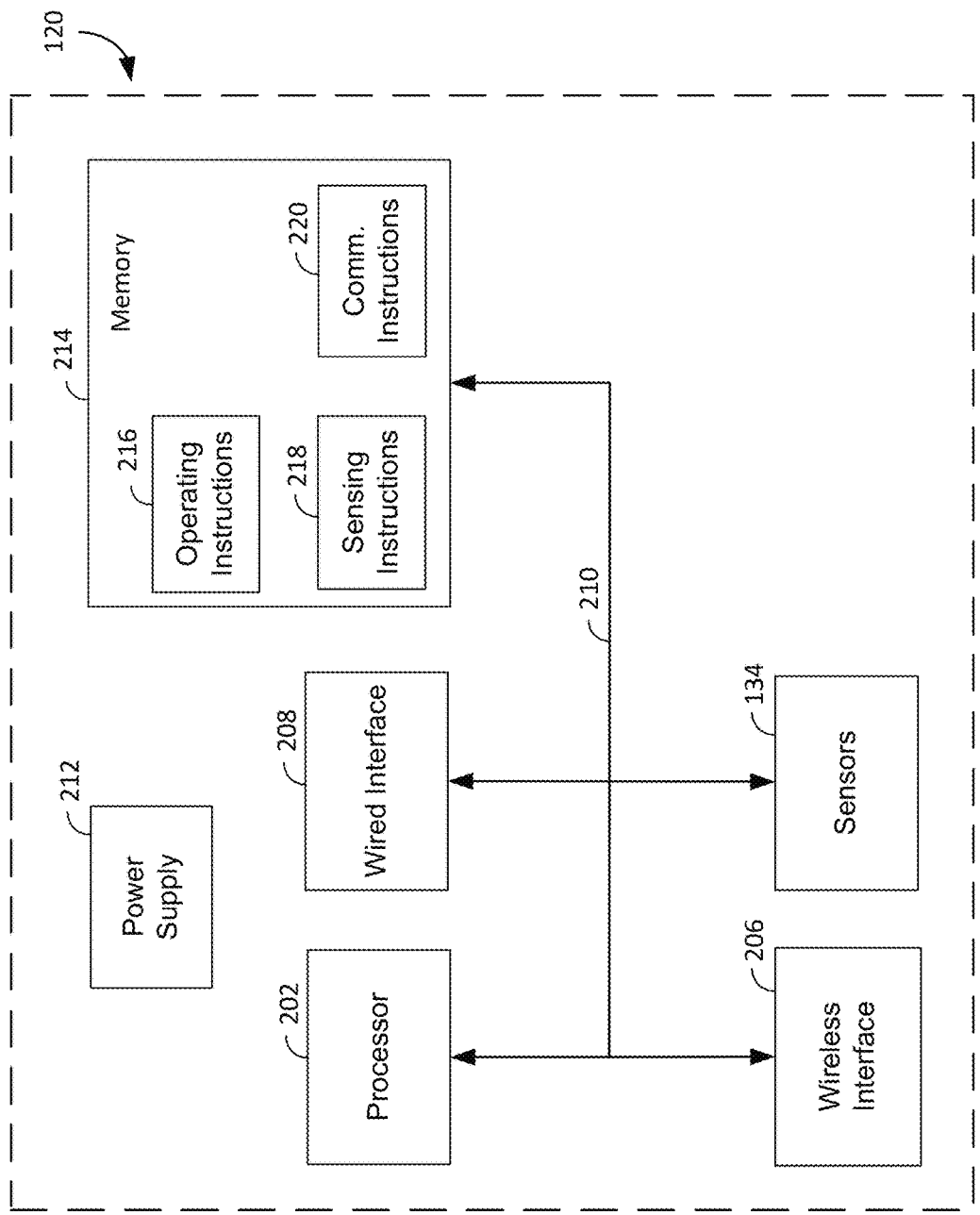
FIG. 8 shows an exemplary remote measurement device in accordance with some embodiments of the present disclosure.

FIG. 8 depicts an exemplary remote measurement device 120 in accordance with some embodiments of the present disclosure. Although remote measurement device 120 may include any suitable components, in one embodiment remote measurement device 120 may include a processor 202, sensors 134, a wireless interface 206, a wired interface 208, internal communication interface 210, a power supply 212, and a memory 214.

Processor 202 may control the operations of the other components of remote measurement device 120, and may include any suitable processor. As described herein, a processor 202 may include any suitable processing device such as a general purpose processor or microprocessor executing instructions from memory, hardware implementations of processing operations (e.g., hardware implementing instructions provided by a hardware description language), any other suitable processor, or any combination thereof. In one embodiment, processor 202 may be a microprocessor that executes instructions stored in memory 214. Memory includes any suitable volatile or non-volatile memory capable of storing information (e.g., instructions and data for the operation and use of remote measurement device 120 and communication network device 122), such as RAM, ROM, EEPROM, flash, magnetic storage, hard drives, any other suitable memory, or any combination thereof.

Processor 202 of remote measurement device 120 may be in communication with sensors 134 via internal communication interface 210. Internal communication interface 210 may include any suitable interfaces for providing signals and data between processor 202 and other components of remote measurement device 120. This may include communication busses such as communication buses such as I²C, SPI, USB, UART, and GPIO. In some embodiments, this may also include connections such that signals from sensors 134 (e.g., measured analog signals) may be provided to processor 202.

Wireless interface 206 may be in communication with processor 202 via the internal communication interface 210, and may provide for wireless communication with other wireless devices such as communication network device 122. Wireless interface 206 may communicate using a standardized wireless communication protocols (e.g., WiFi, ZigBee, Bluetooth, Bluetooth low energy, etc.) or proprietary wireless communication protocol operating at any suitable frequency such as 900 MHz, 2.4 GHz, or 5.6 GHz. In some embodiments, a suitable wireless communication protocol may be selected or designed for the particular signal path between the remote measurement device 120 and communication network device 122. In an embodiment of a remote measurement device 120 implemented with lower valve plate 108, the wireless communication protocol may be selected based on the material properties of the fire hydrant 50 (e.g., cast iron) and the signal path through the interior cavity of the fire hydrant 50 (including when water is provided to fire hydrant 50). In an embodiment of a remote measurement device 120 implemented with a flange insert 140, the wireless communication protocol may be selected based on the transmission path through the soil to the above-ground portion of the fire hydrant 50

Although in some embodiments a remote measurement device 120 may include both a wireless interface 206 and a wired interface 208, in some embodiments only one of the wireless interface 206 or wired interface 208 may be provided. A wired interface 208 may provide an interface with wired connection 125 in order to allow processor 202 to communicate with communication network device 122 as described herein. The wired connection 208 may be any suitable wired connection to facilitate communication via any suitable protocol, as described herein.

Remote measurement device 120 may also include a power supply 212. Power supply may include a connection to an external power supply (e.g., power supplied by wired connection 125), a battery power source, any other suitable power source, or any combination thereof. In some embodiments, power supply 212 may be a replaceable or rechargeable battery such as lithium-ion, lithium-polymer, nickel-metal hydride, or nickel-cadmium battery. The power supply 212 may provide power to the other components of remote measurement device 120.

In one embodiment, memory 214 of remote measurement device may include memory for executing instructions with processor 202, memory for storing data, and a plurality of sets of instructions to be run by processor 202. Although memory 214 may include any suitable instructions, in one embodiment the instructions may include operating instructions 216, sensing instructions 218, and communication instructions 220.

Operating instructions 216 may include instructions for controlling the general operations of the remote measurement device 120. In one embodiment, operating instructions 216 may include instructions for an operating system of the remote measurement device 120, and for receiving updates to software, firmware, or configuration parameters of the remote measurement device 120. In one embodiment, remote measurement device 120 may be a battery-powered device that may be in use for long periods of time without being replaced. Operating instructions 216 may include instructions for limiting power consumption of the remote measurement device 120, for example, by periodically placing some of the components of the remote measurement device 120 into a sleep mode. In one embodiment, the sensors 134 and the communication interface (e.g., wireless interface 206 and/or wired interface 208) may be shut off and a majority of the processing operations of the processor 202 may be shut off. In some embodiments, sensing with sensors 134 may only occur on relatively long intervals (e.g., every few minutes) while the processor 202 may check the communication interface (e.g., wireless interface 206 and/or wired interface 208) more frequently to determine whether data has been requested by the communication network device 122. In other embodiments, sensing with sensors 134 may occur more frequently, and the communication interface (e.g., wireless interface 206 and/or wired interface 208) may only be powered on relatively infrequently (e.g., every few hours), or if a warning or error should be provided based on the measurements from the sensors 134.

Sensing instructions 218 may include instructions for operating the sensors 134 and for processing data from the sensors 134. As described herein, sensors 134 may include a variety of types of sensors that measure a variety of different characteristics of the water. Sensing instructions 218 may provide instructions for controlling these sensors, determining values based on signals or data received from the sensors 134, and performing calculations based on the received signals or data. While in some embodiments, raw sensor data or calculated values may be received or calculated based on the sensing instructions 218, in some embodiments the sensing instructions 218 may also include data analysis such as a comparison with threshold or warning values. For example, if the pressure that is sensed at a pressure sensor of sensors 134 falls below a threshold, sensing instructions 218 may provide for a warning to be provided to communication network device 122. If a chemical or biological content of the water exceeds a threshold parts per million, a warning may be provided to communication network device 122. In some embodiments, sensing instructions 218 may also analyze data trends or perform statistical analysis based on data received from the sensors 134, determine warnings therefrom, and provide the trends, statistics, and/or warnings to the communication network device 122.

Communication instructions 220 may include instructions for communicating with other devices such as communication network device 122. Communications instructions may include instructions for operating the wireless interface 206 and/or wired interface 208, including physical layer, MAC layer, logical link layer, and data link layer instructions to operate the wireless interface 206 and/or wired interface 208 in accordance with a standardized or proprietary communication protocol. Communication instructions 220 may also include instructions for encrypting and decrypting communications between remote measurement device 120 and communication network device 122, such that unauthorized third parties are unable to eavesdrop on such communications. Communication instructions 220 may also include instructions for a message format for communications exchanged between remote measurement device 120 and communication network device 122. The message format may specify message types, such as warning messages, wake up messages, update messages, data upload messages, and data request messages.

Figure 9:
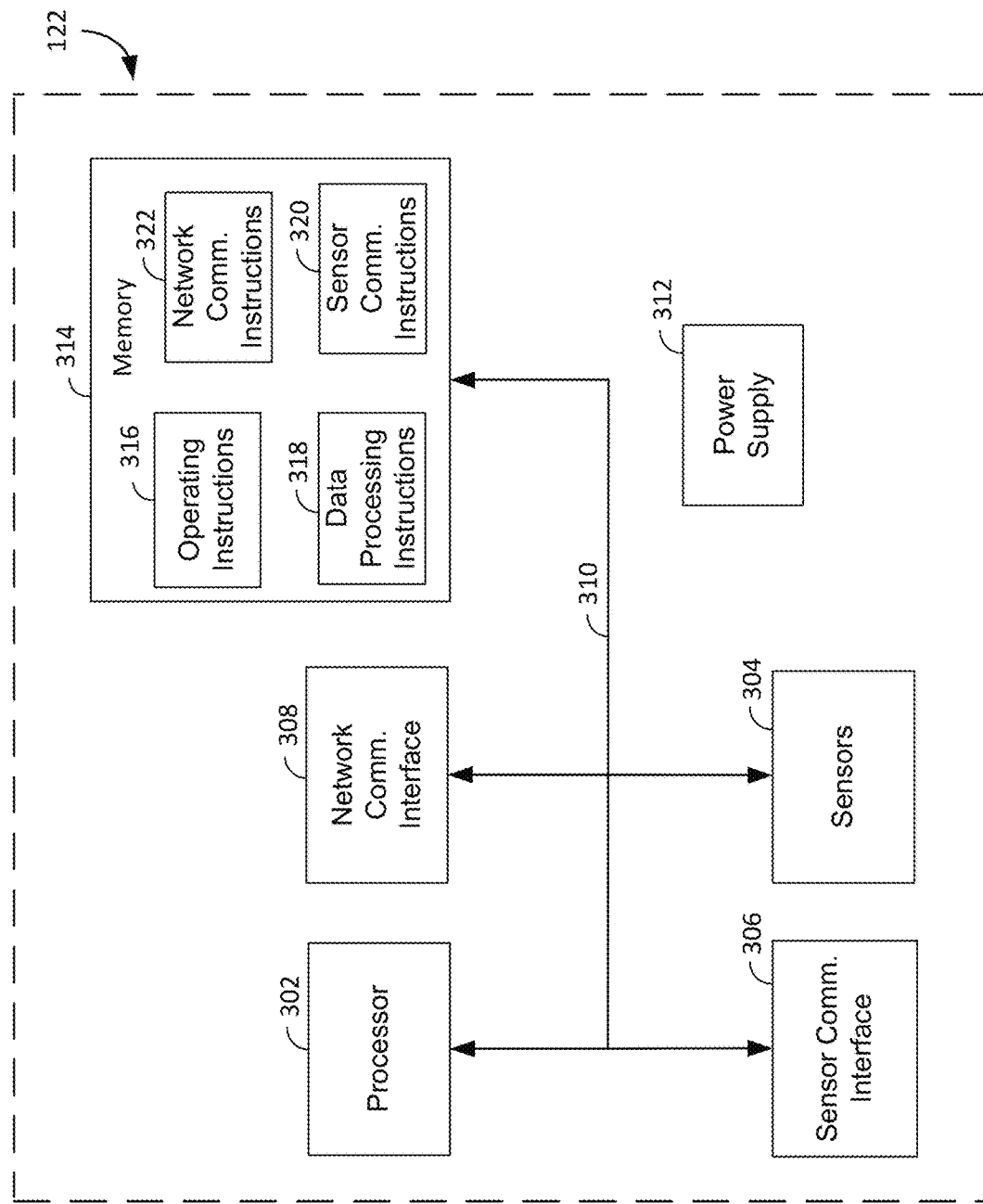
FIG. 9 shows an exemplary communication network device in accordance with some embodiments of the present disclosure.

FIG. 9 shows an exemplary communication network device 122 in accordance with some embodiments of the present disclosure. Although communication network device 122 may include any suitable components, in one embodiment communication network device 122 may include a processor 302, sensors 304, a sensor communication interface 306, a network communication interface 308, internal communication interface 310, power supply 312, and memory 314.

Processor 302 may control the operations of the other components of communication network device 122, and may include any suitable processor. A processor 302 may include any suitable processing device such as a general purpose processor or microprocessor executing instructions from memory, hardware implementations of processing operations (e.g., hardware implementing instructions provided by a hardware description language), any other suitable processor, or any combination thereof. In one embodiment, processor 302 may be a microprocessor that executes instructions stored in memory 314. Memory includes any suitable volatile or non-volatile memory capable of storing information (e.g., instructions and data for the operation and use of communication network device 122), such as RAM, ROM, EEPROM, flash, magnetic storage, hard drives, any other suitable memory, or any combination thereof.

In some embodiments, communication network device 122 may include sensors 304. For example, communication network device 122 may be combined with remote measurement device 120, such that they operate as a single unit. In other embodiments, the sensing operations may be performed directly at network communication device 122, such as when water is provided to communication network device 122 by a pitot tube. In addition, communication network device may sense other characteristics about the location where it is located within fire hydrant 50, such as temperature.

Sensor communication interface 306 may be in communication with processor 302 via the internal communication interface 310, and may provide for wireless or wired communications with remote measurement device 120. In one embodiment, sensor communication interface 306 may include a wireless interface that communicates using a standardized wireless communication protocol (e.g., WiFi, ZigBee, Bluetooth, Bluetooth low energy, etc.) or proprietary wireless communication protocol operating at any suitable frequency such as 900 MHz, 2.4 GHz, or 5.6 GHz. As described herein, a suitable wireless communication protocol may be selected or designed for the particular signal path between the remote measurement device 120 and communication network device 122. In some embodiments, sensor communication interface 306 may be a wired interface that provides an interface with wired connection 125 in order to allow processor 302 to communicate with remote measurement device 120 as described herein. The wired connection 125 may be any suitable wired connection to facilitate communication via any suitable protocol, as described herein.

Network communication interface 308 may be in communication with a communication network for monitoring characteristics of the water distribution system 1. In one embodiment, the network communication interface 308 may provide for communications with a central monitoring system 12, such as by using a cellular communication network or mesh communication network. In an exemplary embodiment of a cellular communication network, the communication network device 122 may communicate in any suitable manner, such as via internet protocol data communications or short message system (SMS) messages. In an exemplary embodiment of a mesh communication system, data may be transmitted to the central monitoring system 12 via the mesh network or using a data collection procedure (e.g., using a service vehicle to survey the communication network devices 122 at fire hydrants 50).

Communication network device 122 may also include a power supply 312. Power supply 312 may include a connection to an external power supply (e.g., power supplied by a utility system), a battery power source, any other suitable power source, or any combination thereof. In some embodiments, power supply 312 may be a replaceable or rechargeable battery such as lithium-ion, lithium-polymer, nickel-metal hydride, or nickel-cadmium battery. The power supply may provide power to the other components of communication network device 122.

In one embodiment, memory 314 of communication network device 122 may include memory for executing instructions with processor 302, memory for storing data, and a plurality of sets of instructions to be run by processor 302. Although memory 314 may include any suitable instructions, in one embodiment the instructions may include operating instructions 316, data processing instructions 318, sensor communication instructions 320, and network communication instructions 322.

Operating instructions 316 may include instructions for controlling the general operations of the communication network device 122. In one embodiment, operating instructions may include instructions for an operating system of the communication network device 122, and for receiving updates to software, firmware, or configuration parameters of the communication network device 122. In one embodiment, communication network device 122 may be a battery-powered device that may be in use for long periods of time without being replaced. Operating instructions 316 may include instructions for limiting power consumption of the communication network device 122, for example, by periodically placing some of the components of the communication network device 122 into a sleep mode. In one embodiment, the sensors 304 and the communication interfaces (e.g., sensor communication interface 306 and network communication interface 308) may be shut off and a majority of the processing operations of the processor 302 may be shut off. The communication interfaces may wake up on a periodic basis to check for messages from the remote measurement device 120 or the communication network. In some embodiments, the wake up times may be scheduled based on messages from one or more of the central monitoring system 12, remote measurement device 120, and/or communication network device 122. In some embodiments, communication network device 122 may not enter the sleep mode while processing certain information such as warning messages or error messages (e.g., to monitor more frequently based on the occurrence of an error or warning).

Data processing instructions 318 may include instructions for processing data that is received from the remote measurement device 120 via the sensor communication interface 306. As described herein, the sensors 304 of the remote measurement device may measure characteristics such as pressure, turbidity, temperature, heave, material content (e.g., total dissolved solids), biological content, chemical content (e.g., chlorine), or any other suitable characteristics. The data processing instructions 318 may process this data to determine warnings, monitor data trends, calculate statistics, or perform any other suitable data processing operations as described herein. In one embodiment, data processing instructions 318 may include instructions for monitoring the change in water pressure over time, and based on identified changes, may provide messages such as warning messages to central monitoring system 12.

Sensor communication instructions 320 may include instructions for communicating with remote measurement device 120. Sensor communications instructions may include instructions for operating the sensor communication interface 306, including physical layer, MAC layer, logical link layer, and data link layer instructions in accordance with a standardized or proprietary communication protocol. Sensor communication instructions 320 may also include instructions for encrypting and decrypting communications between remote measurement device 120 and communication network device 122, such that unauthorized third parties are unable to eavesdrop on such communications. Sensor communication instructions 220 may also include instructions for a message format for communications exchanged between communication network device 120 and communication network device 122. The message format may specify message types, such as warning messages, wake up messages, update messages, data upload messages, and data request messages.

Network communication instructions 322 may include instructions for communicating with a communication network such as a cellular network and/or mesh network. In one embodiment, network communication instructions 322 may include instructions for communicating on a cellular network using an internet protocol data format or a SMS data format. Network communication instructions 322 may also include instructions for communicating using a mesh network (e.g., ZigBee). Communication instructions 320 may also include instructions for encrypting and decrypting communications between communication network device 122 and the communication network, such that unauthorized third parties are unable to eavesdrop on such communications. Communication instructions 320 may also include instructions for a message format for communications exchanged between communication network device 122 and the communications network. The message format may specify message types, such as warning messages, wake up messages, update messages, data upload messages, and data request messages.

Figure 10:
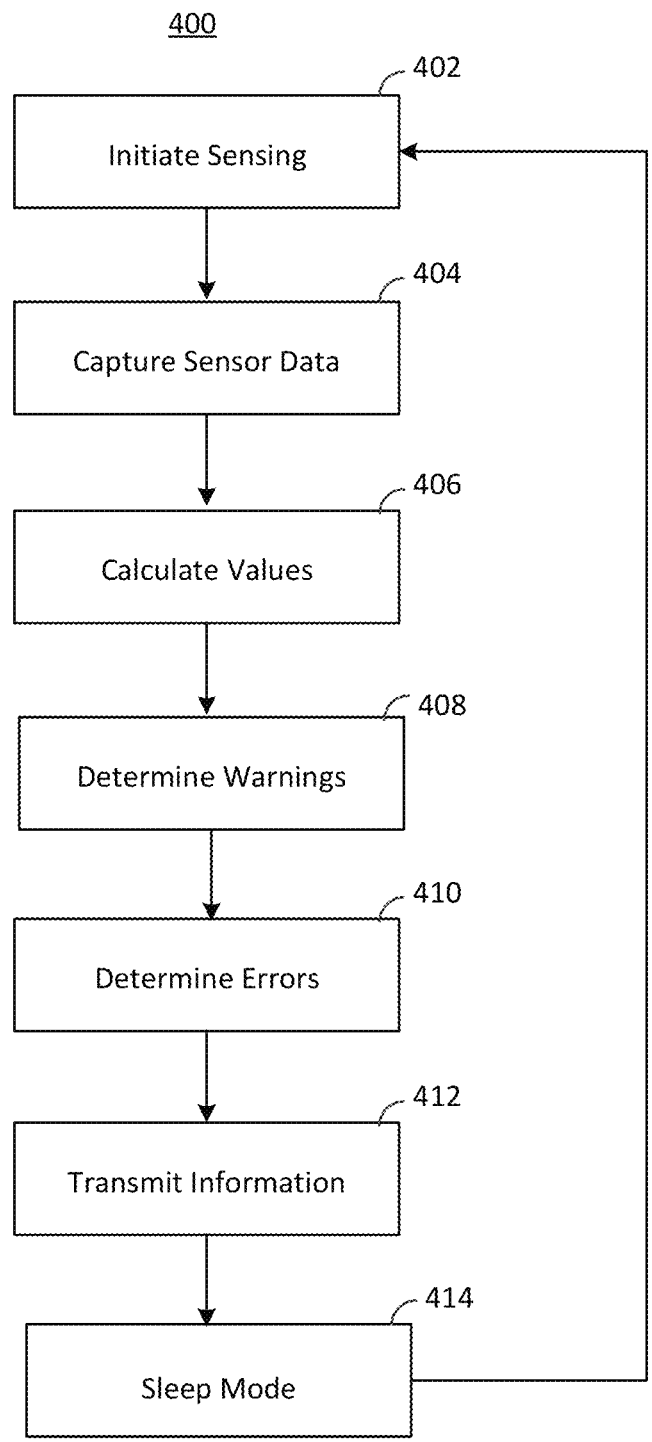
FIG. 10 depicts a non-limiting flow diagram illustrating exemplary methods for operating a remote measurement device in accordance with some embodiments of the present disclosure.

FIG. 10 depicts a non-limiting flow diagram illustrating exemplary methods for operating a remote measurement device 120 in accordance with some embodiments of the present disclosure. Although a particular series of steps 400 are depicted as being performed in a particular order in FIG. 10, it will be understood that one or more steps may be removed or added, and the order of the steps may be modified in any suitable manner. In one embodiment, processing of steps 400 may begin at step 402.

At step 402, remote measurement device 120 may initiate sensing of characteristics of the water flowing through the water main 14. In one embodiment, remote measurement device 120 may be in a sleep mode and may periodically provide power to the sensors. In some embodiments, the sensors 134 may be activated in response to another stimulus such as a message from communication network device 122. Processing may then continue to step 404.

At step 404, remote measurement device 120 may capture sensor data from its sensors 134. The sensors 134 may be located at the surface of remote measurement device 120, at or in a channel of the remote measurement device 120, at or in a reservoir of the remote measurement device 120, or at any other suitable location in contact with the water in the shoe 124. The sensors 134 may provide signals that may be processed by a processor 202 of the remote measurement device 120 (e.g., an analog signal representative of a value of the sensed characteristic) and/or may provide a data signal (e.g., digital data representative of the sensed characteristic). The captured data may be stored in memory 214 of the remote measurement device 120. Processing may continue to step 406.

At step 406, the processor 202 of the remote measurement device 120 may calculate values from the received data. The values may be determined based on applying processing to a received signal (e.g., a received analog signal), based on a received data signal, based on performing calculations relating to a plurality of sensed characteristics, in any other suitable manner, or any combination thereof. In some embodiments, statistics, data trends, and other similar values may also be calculated and stored in memory 214. Processing may continue to step 408.

At step 408, the processor 202 of the remote measurement device 120 may determine whether there are any warnings associated with the measured data and/or calculated values for the characteristics. Warnings may include conditions that relate to problems with the water distribution system, such as water pressure issues and water quality issues (e.g., turbidity, solid content, chemical content, biological content, etc.). Although warnings may be determined in any suitable manner, in some embodiments the warnings may be based on a comparison of values with thresholds, a rate of change for values, or a combination of values that is indicative of a particular water condition. The warnings may be stored in memory 214. Once the warnings are determined at step 408, processing may continue to step 410.

At step 410, the processor 202 of the remote measurement device 120 may determine whether there are any errors associated with the measured data and/or calculated values for the characteristics. Errors may relate to the functioning of the remote measurement device 120 (e.g., a failed sensor or low battery) or the fire hydrant 50 (e.g., a failed component such as a seal). Although errors may be determined in any suitable manner, in some embodiments the errors may be determined based on one or more of the measurements or calculated values not being within an acceptable range, or based on a combination of values indicating an error (e.g., a failed seal). The errors may be stored in memory 214. Once the errors are determined at step 410, processing may continue to step 412.

At step 412, the information that is determined by the remote measurement device 120 (e.g., values for characteristics, warnings, and errors) may be transmitted to another device (e.g., the communication network device 122) via a suitable interface (e.g., a wireless and/or wired interface). In one embodiment, the information may be transmitted during each sensing period that is initiated at step 402. In some embodiments, the information may be transmitted less frequently in the absence of a warning or error. Whether a warning or error is transmitted may also be based on the warning or error type or the severity. Once the information is transmitted, processing may continue to step 414.

At step 414, the remote measurement device 120 may enter a sleep mode. In some embodiments, the parameters for the sleep mode such as sleep time may be based on communications with another device such as the communication network device 122. During the sleep mode, many of the powered components of the remote measurement device 120 such as the sensors 134 and communication interface may not receive power. In some embodiments, certain components (e.g., a pressure sensor) may continue to receive power during the sleep mode in order to determine if there are any critical warnings. Once the sleep mode is entered, processing may return to step 402.

Figure 11:
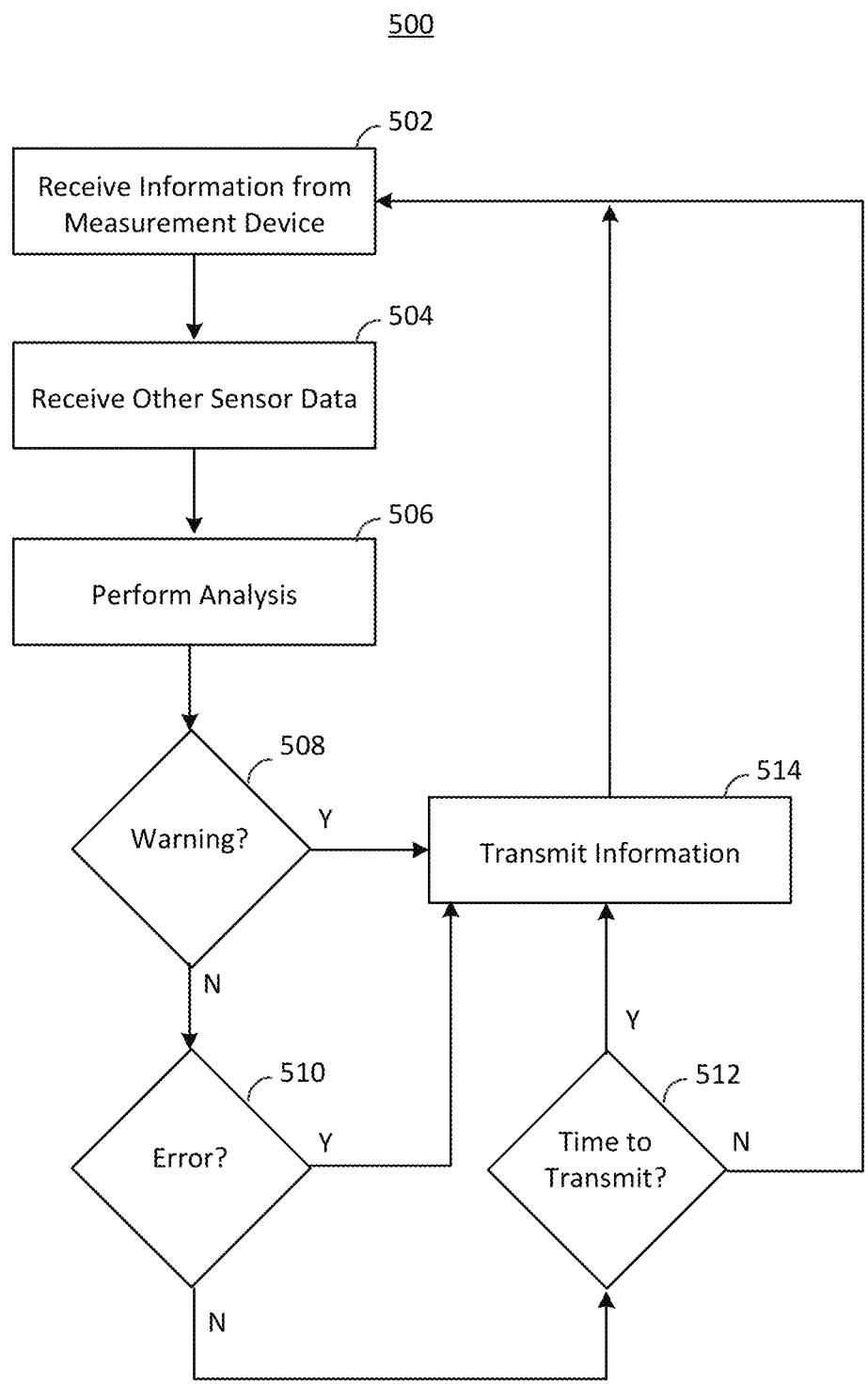
FIG. 11 depicts a non-limiting flow diagram illustrating exemplary methods for operating a communication network device in accordance with some embodiments of the present disclosure.

FIG. 11 depicts a non-limiting flow diagram illustrating exemplary methods for operating a communication network device 122 in accordance with some embodiments of the present disclosure. Although a particular series of steps are depicted as being performed in a particular order in FIG. 11, it will be understood that one or more steps may be removed or added, and the order of the steps may be modified in any suitable manner. In one embodiment, processing of steps 500 may begin at step 502.

At step 502, information may be received at the communication network device 122 via a communication interface in communication with the remote measurement device 120. In some embodiments, the communication network device 122 may be in a sleep mode, and may periodically exit the sleep mode (e.g., at predetermined times) to receive messages from the remote measurement device 120. In other embodiments, the sensor communication interface of the communication network device 122 may remain active, and when a message is received, other circuitry and/or functionality of the communication network device may be enabled. Although not depicted herein, in some embodiments there may be a plurality of remote measurement devices 120 located at different locations within the fire hydrant (e.g., one device located within the path of the water main 14, and another remote measurement device located within a barrel of the fire hydrant 50, such that the operation of the valve may be monitored). Once the information has been received at step 502, processing may continue to step 504.

At step 504, the communication network device 122 may receive other sensor data, such as from a local sensor of the communication network device 122. Local sensor data may include any suitable data such as environmental data (e.g., temperature) or data relating to the operation of the communication network device 122. Once the local sensor data has been received at step 504, processing may continue to step 506.

At step 506, the processor 302 of the communication network device 122 may analyze the received information and data to determine data values, warnings, errors, or other suitable values or indications. In some embodiments, the analysis may include the determination of data trends or statistics relating to the received information and values. As described herein, warnings may include conditions that relate to problems with the water distribution system, such as water pressure issues and water quality issues (e.g., turbidity, solid content, chemical content, biological content, etc.), and may be determined in any suitable manner (e.g., based on a comparison of values with thresholds, a rate of change for values, or a combination of values that is indicative of a particular water condition). Errors may relate to the functioning of the remote measurement device 120 or communication network device 122 (e.g., a failed sensor or low battery) or the fire hydrant 50 (e.g., a failed component such as a seal). Although errors may be determined in any suitable manner, in some embodiments the errors may be determined based on one or more of the measurements or calculated values not being within an acceptable range, or based on a combination of values indicating an error. The results of the analysis may be stored in memory at step 506, and processing may continue to step 508.

It may be desired to transmit data to the communication network (e.g., to the central processing system 12) on an occasional basis, in order to limit power consumption of the communication network device 122, transmission costs, and to prevent excess traffic over the communication network. Accordingly, steps 508-514 may determine when data is to be transmitted by the communication network device 122.

At step 508, it may be determined whether a warning was identified by the remote measurement device 120 or the communication network device 122. If a warning was identified, processing may continue to step 514. If a warning was not identified, processing may continue to step 510.

At step 510, it may be determined whether an error was identified by the remote measurement device 120 or the communication network device 122. If an error was identified, processing may continue to step 514. If an error was not identified, processing may continue to step 512.

At step 512, it may be determined whether it is time to transmit to the communication network. In one embodiment, the communication network device 122 may transmit on a periodic basis. In some embodiments, the communication network device 122 may also transmit based on some other trigger such as a request for data from the central processing system 12 or another device of a mesh network. If it is time to transmit, processing may continue to step 514. If it is not time to transmit, processing may return to step 502.

At step 514, information may be transmitted by the communication network device 122. As described herein, the information may be transmitted via any suitable communication method such as a cellular network or a wireless mesh network. The information may be transmitted according to a message format for the communication network, and may eventually be provided to the central monitoring system. Based on information received from communication network devices 122 located at fire hydrants 50 throughout the water distribution system 1, problems with the water distribution system 1 can be quickly identified and localized, and resources deployed to remedy any such problems. Once the information is transmitted at step 514, process may return to step 502.

In another embodiment, the remote monitoring device 120 can include an acoustic hydrophone as one of the sensors 134 that is incorporated into the lower valve plate 108 of the main valve. The acoustic hydrophone can be used for leak detection in the water distribution system 1.

Figure 12A:
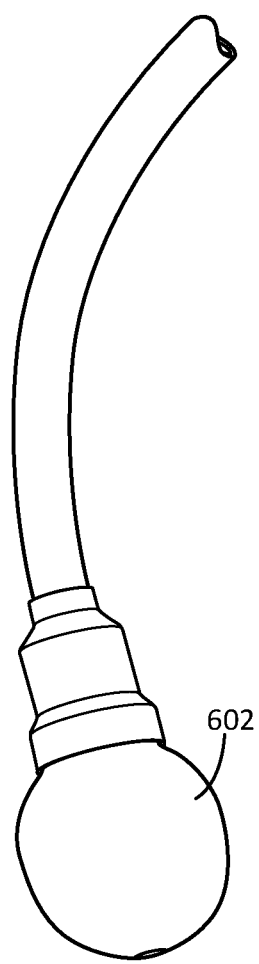
FIGS. 12A and 12B show acoustic hydrophones in accordance with some embodiments of the present disclosure.
Figure 12B:
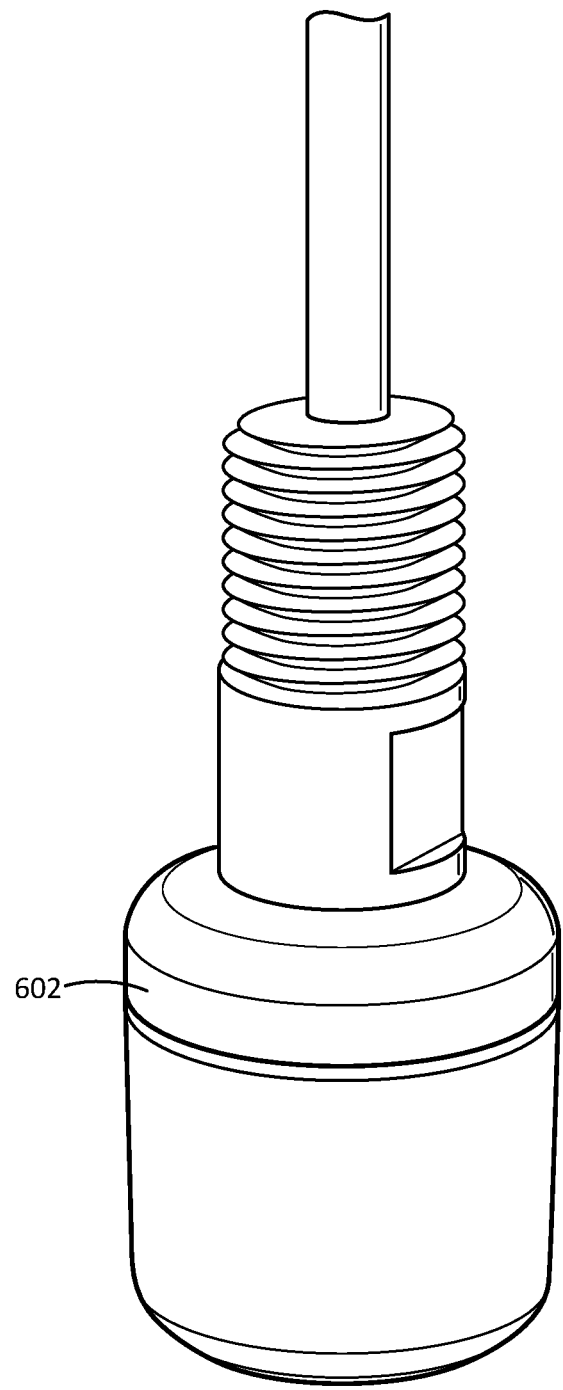

FIGS. 12A and 12B show different embodiments of acoustic hydrophones 602 that can be used in the present disclosure. While two different embodiments of acoustic hydrophones 602 are shown, it is to be understood that any suitable acoustic hydrophone can be used in the present disclosure. The acoustic hydrophone 602 can be placed in contact with water in the shoe 124 of the hydrant 50 and can collect an analog sound spectrum transmitted through the water across a specific frequency range, similar to a microphone. The acoustic hydrophone 602 can provide more accurate acoustic information than a hydrant-body based acoustic sensor that measures vibrations in the iron of the hydrant. The use of different materials (e.g., plastic versus ductile) in the pipes of the water distribution system 1 and water mains 14, especially if used inconsistently (i.e., mixed and matched), can result in less accurate measurements from a hydrant-body-based acoustic sensor.

In one embodiment, the acoustic hydrophone 602 can include a piezoelectric element to sense leak-induced sound or vibration. The acoustic hydrophone 602 can also include signal amplifiers and/or noise filters to improve the signal with the acoustic information from the acoustic hydrophone 602.

Figure 13:
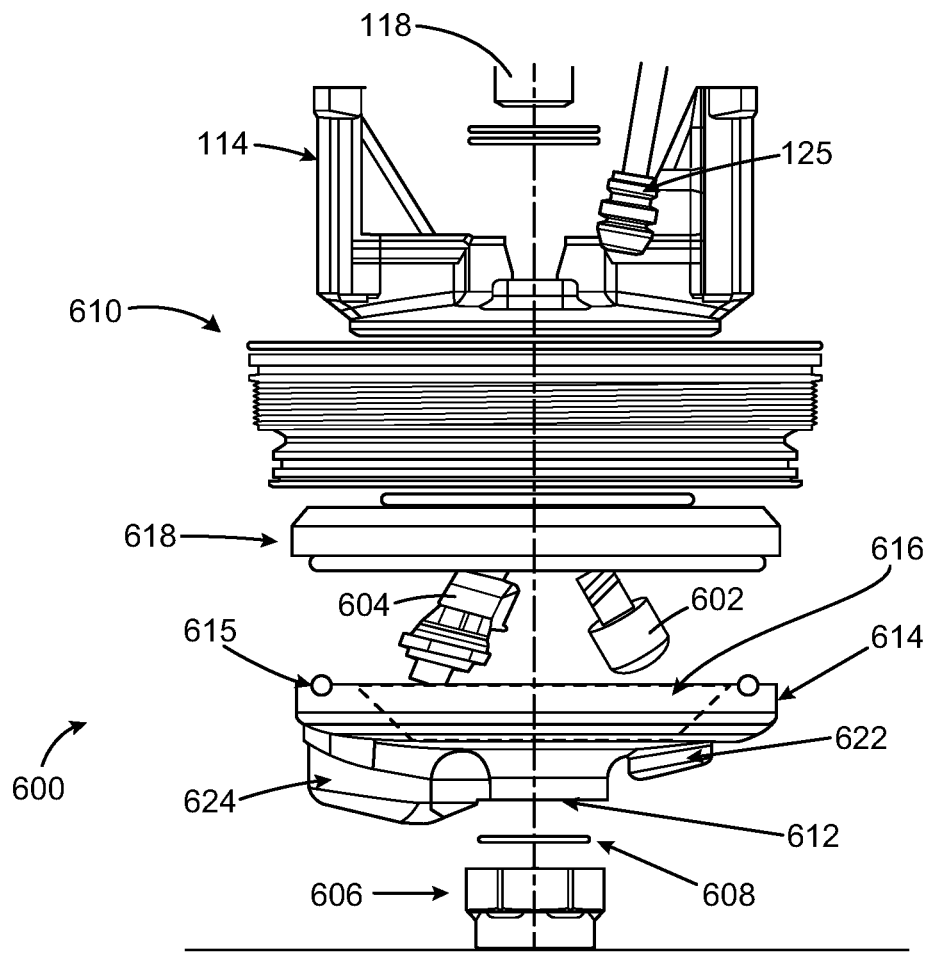
FIG. 13 shows an exploded view of the main valve with an acoustic hydrophone in accordance with an embodiment of the present disclosure.
Figure 14:
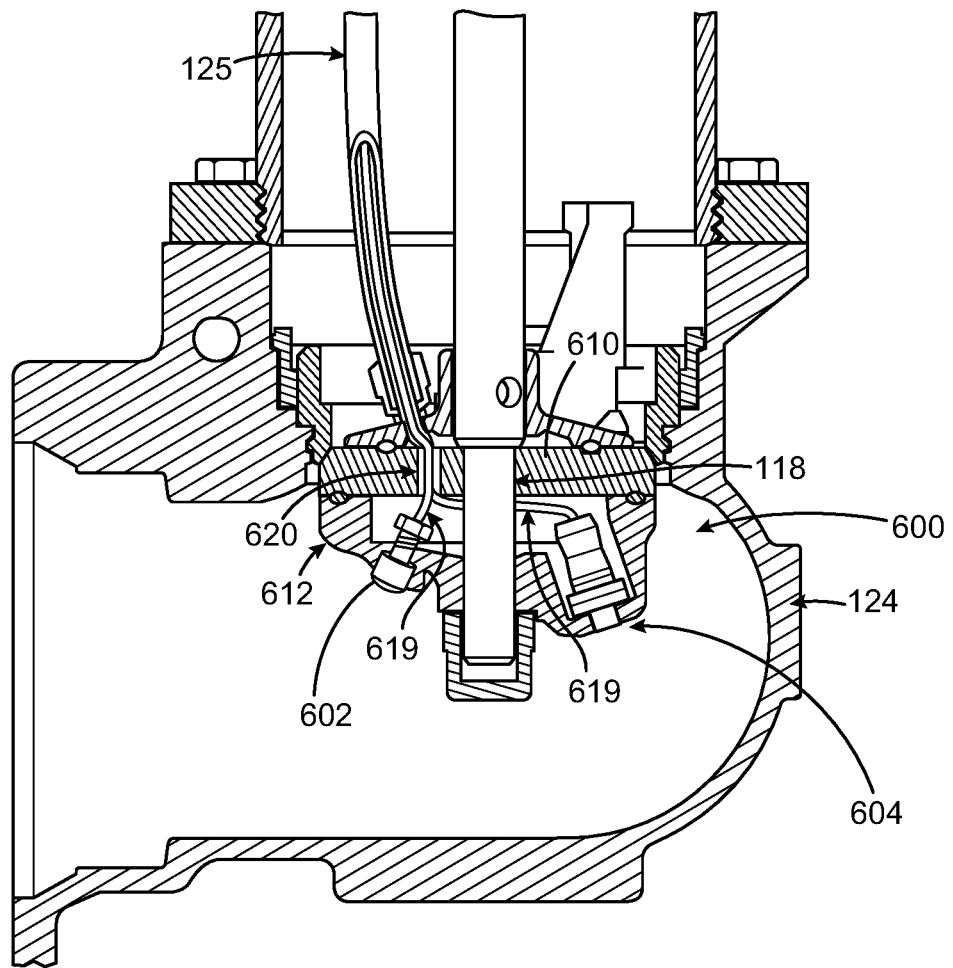
FIG. 14 shows a partial cross-sectional view of the lower portion of the hydrant and shoe in accordance with an embodiment of the present disclosure.

FIGS. 13 and 14 show an embodiment of the acoustic hydrophone 602 with respect to a lower valve assembly (or main valve). FIG. 13 shows an exploded view of an embodiment of a lower valve assembly 600, while FIG. 14 shows an embodiment of the lower valve assembly 600 in a shoe 124 of the hydrant 50. In the embodiment of FIGS. 13 and 14, the acoustic hydrophone 602 can be used in conjunction with a pressure sensor 604 that is also incorporated in the lower valve assembly 600. In still other embodiments, a temperature sensor (not shown) may also be incorporated in the lower valve assembly and used in conjunction with the acoustic hydrophone 602 and/or the pressure sensor 604. The acoustic hydrophone 602 and the pressure sensor 604 can be connected to the remote monitoring device 120, which may be located in an upper portion of the hydrant 50, by the wired connection 125 in one embodiment. In another embodiment, the remote monitoring device 120 may be located in the lower valve assembly 600.

The lower valve assembly 600 can be connected to the shaft 118 by a lock nut 606 in one embodiment. An O-ring 608 can be used with the lock-nut 606 to provide a waterproof connection between the shaft 118 and the lock nut 606. The lower valve assembly 600 can include an upper plate 610 connected to a bottom plate 612. The bottom plate 612 can have a lower portion 614 with a cavity 616 therein and an upper portion 618 that can be positioned on the lower portion 614 to enclose the cavity 616 in the bottom plate 612. In one embodiment, an O-ring 615 or other suitable mechanism can be positioned between the upper portion 618 and the lower portion 614 to form a waterproof seal between the upper portion 618 and the lower portion 614. The pressure sensor 604 and the acoustic hydrophone 602 can be located in the cavity 616. At least a portion of the pressure sensor 604 can extend through the lower portion 614 of the bottom plate 612 and into contact with the water in the shoe 124. The pressure sensor 604 can be positioned in a pressure sensor enclosure 624 to provide some protection to the pressure sensor 604 and ensure that the pressure sensor 604 is oriented properly. Similarly, the acoustic hydrophone 602 can extend through the lower portion 614 of the bottom plate 612 and into contact with the water in the shoe 124. The acoustic hydrophone 602 can be positioned in a hydrophone enclosure 622 to provide some protection to the acoustic hydrophone 602 and ensure that the hydrophone 602 is oriented properly.

The corresponding wires 619 from the acoustic hydrophone 602 and the pressure sensor 604 can pass through corresponding passageways (or openings) in the upper portion 618 of the bottom plate 612 (not shown) and passageways (or openings) 620 in the upper plate 610 and travel to the upper portion of the hydrant 50 via wired connection 125. In one embodiment, the passageway 620 in the upper plate 610 may include a rubber seal to prevent water from entering the upper plate 610 and cavity 616 while still permitting the wire(s) 619 to pass through the upper plate 610 to the wired connection 125. The wires 619 may either be connected to wired connection 125 or form a part of the wired connection 125. In one embodiment, the wire 619 from the acoustic hydrophone 602 may be a coaxial cable.

Figure 15:
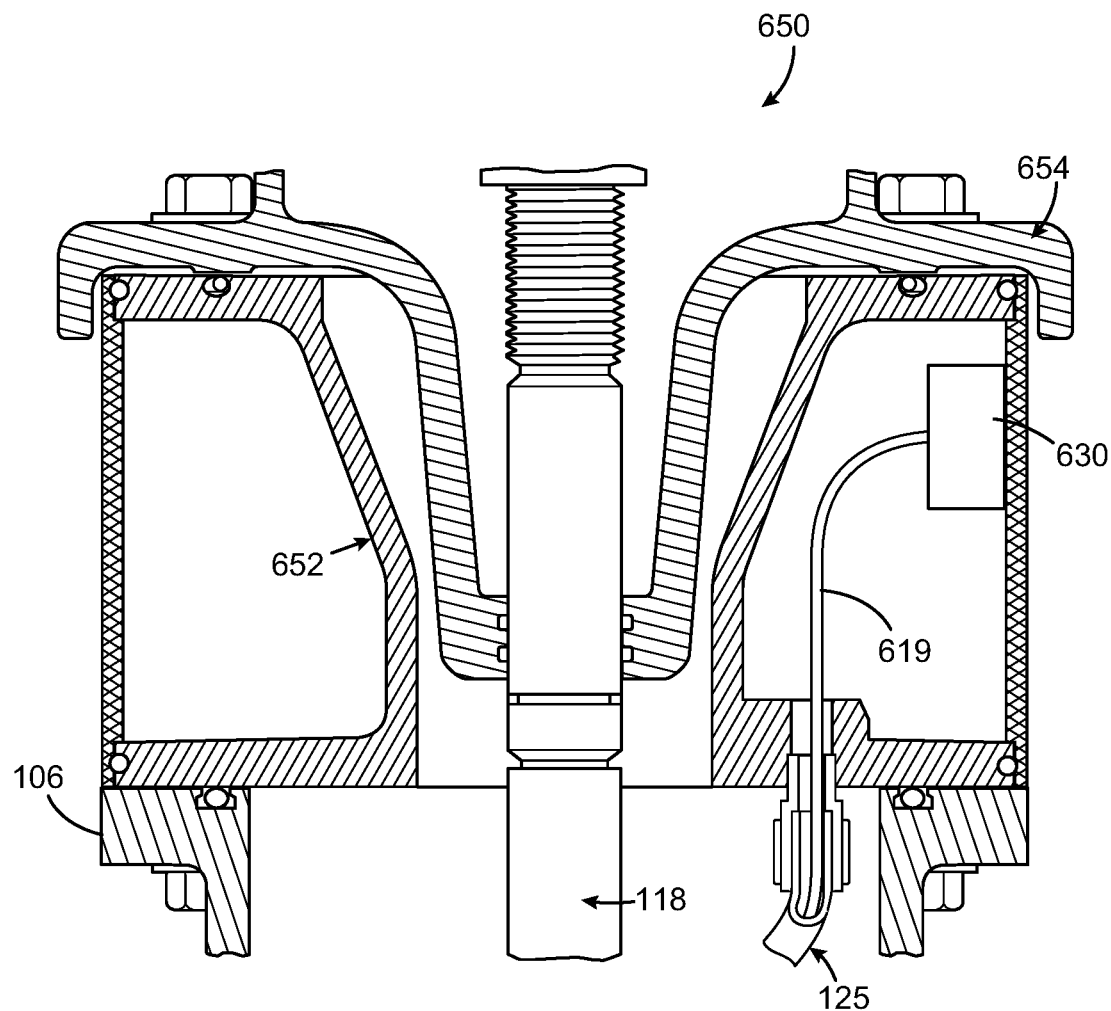
FIG. 15 shows a partial cross-sectional view of the upper portion of the hydrant in accordance with an embodiment of the present disclosure.

FIG. 15 shows an embodiment of the upper portion of the hydrant 50. The upper portion 650 of the hydrant 50 can include an upper portion of the barrel 106, a bonnet 654 connected to the shaft 118 and a spool 652 located between the bonnet 654 and the upper portion of the barrel 106. The wired connection 125 can be connected to a passageway (or opening) in the spool 652. In one embodiment, the passageway in the spool 652 may include a rubber seal to prevent water from entering the spool 652 while still permitting the wire(s) 619 to pass through the spool 652 to the communication device 630. One or more wires 619 from the wired connection 125 can be connected to a communication device 630 located in the spool 652 of the upper barrel 650. The communication device 630 can include a microprocessor and communication equipment (such as a transceiver or cellular equipment) to permit the communication device 630 to communicate with the central monitoring system 12 and process signals and/or data from the acoustic hydrophone 602 and the pressure sensor 604. In one embodiment, the communication device 630 can incorporate the communication network device 122 and/or the remote monitoring device 120. Each of the hydrants 50 in the water distribution system 1 (or a subset thereof) can communicate the acoustic information from the acoustic hydrophone 602 to the central monitoring system 12.

In one embodiment, the acoustic hydrophone 602 can continuously collect the acoustic information from the water corresponding to the analog sound spectrum. However, in other embodiments, the hydrophone 602 can intermittently collect information from the water corresponding to the analog sound spectrum at predetermined intervals or at random times. The collected acoustic information (which can be representative of leak induced vibration or sound) can be digitized by an analog to digital circuit on a circuit board of the communication device 630 before being transmitted to the central monitoring system 12. In another embodiment, the collected acoustic information can be digitized by an analog to digital circuit in the remote monitoring device 120 and then provided to the communication device 630 for transmission to the central monitoring system. In one embodiment, the communication device 630 can include one or more memory devices to store the digitized sound spectrum information (i.e., the acoustic information) at the communication device 630 for some rolling period of time (e.g., last 24 hours) before transmitting the information to the central monitoring system 12. In another embodiment, the communication device 630 can provide the acoustic information stored in the memory devices to the central monitoring system 12 in response to a request from the central monitoring system 12.

The central monitoring system 12 can process the digitized acoustic information from one or more hydrants 50 to determine if a leak is present in the water distribution system. In one embodiment, the digitized acoustic information sample from one hydrant 50 is tightly time synchronized with other acoustic information samples from different hydrants 50 (often using a global positioning system (GPS) time sync signal as captured at each hydrant 50). A Fast Fourier Transform (FFT) mathematical method can be applied to the acoustic information samples collected (or received) from multiple hydrants 50 to show, usually graphically, how the same noise pattern appears at multiple locations. Both the frequency profile and the amplitude of the signal from the FFT often indicates the nature and size of the leak, and the difference in amplitude of a same frequency profile as observed from different locations can indicate how relatively near or far the leak is from a particular hydrant 50.

In another embodiment, a cross-correlation method can be applied to the acoustic information to find a time lag between acoustic information from neighboring hydrants 50. The time lag information can be used to determine the location of the leak between the hydrants 50.

In an embodiment, the acoustic hydrophone 602 and the pressure sensor 604 can operate in conjunction to determine possible leaks in the water distribution system. For example, pressure drops or declines detected by the pressure sensor 604 can be associated with corresponding increases in acoustic "noise" from the acoustic hydrophone 602 to indicate a leakage in the water distribution system 1.

In other embodiments, the acoustic hydrophone 602 can be mounted in the shoe 124 (e.g., adhered to the inside wall of the shoe 124) in place of the lower valve assembly 600. In a further embodiment, the acoustic hydrophone 602 can be mounted in the barrel 106 of the hydrant 50 (e.g., in or near the plug(s) of the hydrant), if the hydrant 50 is configured as a wet-barrel hydrant (see FIG. 16) or if the lower valve assembly 600 is open to permit water to reach the acoustic hydrophone 602.

Figure 18:
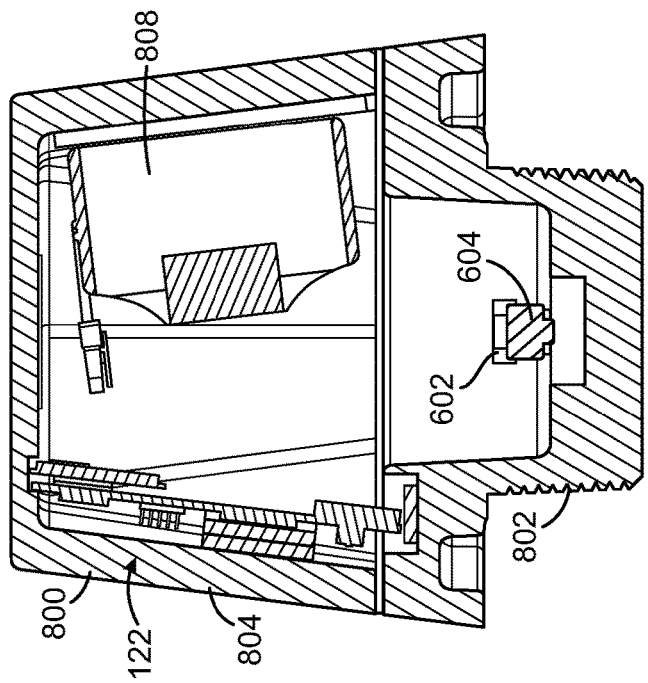
FIG. 18 shows a cross-sectional view of the cap of FIG. 17 taken along line 18-18.
Figure 16:
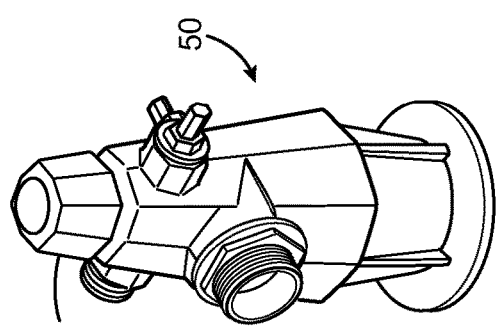
FIG. 16 shows an embodiment of a wet-barrel hydrant.
Figure 17:
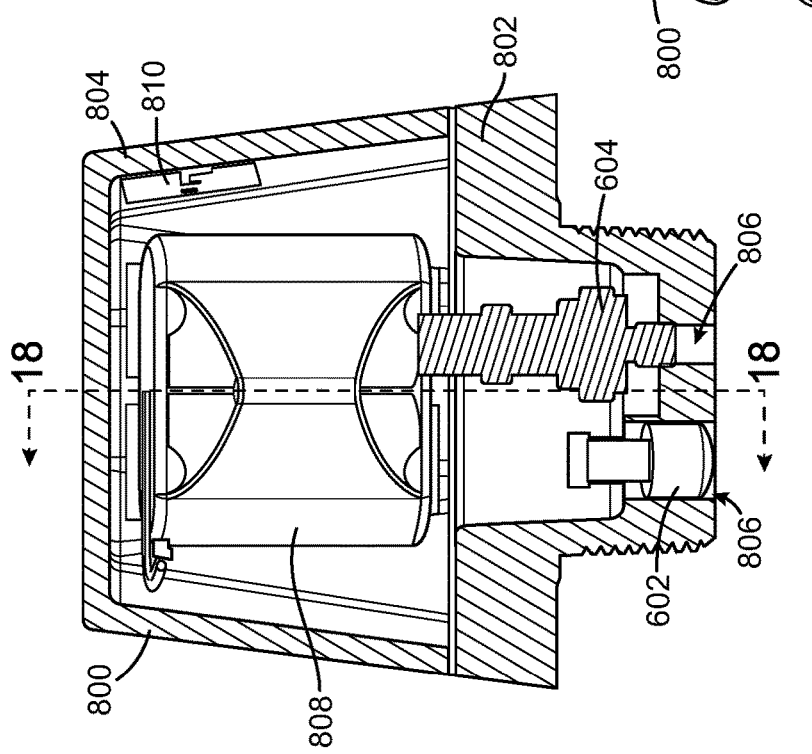
FIG. 17 shows a cross-sectional view of the cap from the wet-barrel hydrant from FIG. 16.

In a further embodiment as shown in FIGS. 16-18, the acoustic hydrophone 602 and pressure sensor 604 may be incorporated in a cap 800 of a wet-barrel hydrant 50. In FIGS. 17 and 18, the cap 800 can have a plug 802 connected to a canister 804 by one or more mechanical fasteners (not shown). In one embodiment, the mechanical fasteners can be screws or bolts, but other types of fasteners or fastening techniques can be used in other embodiments. A sealing device (e.g., a gasket) may be placed between the plug 802 and the canister 804 prior to connecting the plug 802 and canister 804 to provide a water-tight seal. The acoustic hydrophone 602 and the pressure sensor 604 can be located in a cavity of the plug 802. Each of the acoustic hydrophone 602 and the pressure sensor 604 can be partially located in a passageway 806 of the plug 802 such that the acoustic hydrophone 602 and the pressure sensor 604 are in contact with the water in the barrel of the wet-barrel hydrant 50. In one embodiment, the acoustic hydrophone 602 and the pressure sensor 604 can be mounted in appropriate housings or have appropriate seals to prevent water from entering the cavity of the plug 802 via the passageways 806.

In addition, the acoustic hydrophone 602 and the pressure sensor 604 may be connected to the communication network device 122 by a wired connection (not shown). The wired connection can provide a communication path between the communication network device 122 and the acoustic hydrophone 602 and the pressure sensor 604. The communication path provided by the wired connection can be used to communicate sensor signals, which may be analog or digital, from acoustic hydrophone 602 and the pressure sensor 604 and to communicate data signals between communication network device 122 and the acoustic hydrophone 602 and the pressure sensor 604. In an embodiment, the acoustic hydrophone 602 and/or the pressure sensor 604 may process some or all of their measurements and communicate values determined therefrom to communication network device 122 via a data signal. The wired connection may also be used to provide power to the acoustic hydrophone 602 and the pressure sensor 604 from a power supply 808. The wired connection may provide power directly from the power supply 808 to the acoustic hydrophone 602 and the pressure sensor 604 or the power may be provided from the power supply 808 via the communication network device 122. The communication network device 122 may be connected to an antenna 810 to permit the communication network device 122 to communicate with the monitoring system 12 or other hydrants 50.

In an embodiment of the hydrant 50 incorporating the temperature sensor, the temperature sensor can be used to determine a) whether the water is too warm such that disinfectant may fail too quickly; b) whether the water is too cold such that frozen pipes and hydrants could occur; or c) whether the water temperature has changed suddenly, indicating a different flow of water and possibly pipe joint expansion or contraction which could result in new or growing leaks. If none of the above uses are of particular interest to the operator of the water distribution system 1, then the temperature sensor may be omitted and the acoustic hydrophone 602 can be used for leak detection.

The foregoing is merely illustrative of the principles of this disclosure and various modifications may be made by those skilled in the art without departing from the scope of this disclosure. The embodiments described herein are provided for purposes of illustration and not of limitation. Thus, this disclosure is not limited to the explicitly disclosed systems, devices, apparatuses, components, and methods, and instead includes variations to and modifications thereof, which are within the spirit of the attached claims.

The systems, devices, apparatuses, components, and methods described herein may be modified or varied to optimize the systems, devices, apparatuses, components, and methods. Moreover, it will be understood that the systems, devices, apparatuses, components, and methods may have many applications such as monitoring of liquids other than water. The disclosed subject matter should not be limited to any single embodiment described herein, but rather should be construed according to the attached claims.

What is claimed is:

1. A system to monitor water of a water distribution system at a valve of a fire hydrant, the system comprising:
    a valve plate having a sealing surface and an exposed surface in contact with the water;
    a remote measurement system, wherein the remote measurement system comprises:
        at least one acoustic hydrophone located at the exposed surface of the valve plate and configured to measure for acoustic disturbances in the water and provide an electrical signal representative of leak induced vibration or sound; and
        a communication interface coupled to the at least one acoustic hydrophone to receive the electrical signal from the at least one acoustic hydrophone, the communication interface configured to transmit leak induced vibration or sound information based on the received electrical signal from the at least one acoustic hydrophone to a monitoring system, wherein the monitoring system is configured to determine a leak based on the leak induced vibration or sound information.

2. The system of claim 1, wherein the acoustic hydrophone continuously measures for acoustic disturbances in the water.

3. The system of claim 1, wherein the acoustic hydrophone intermittently measures for acoustic disturbances in the water.

4. The system of claim 3, wherein the intermittent measurements of acoustic disturbances occur either randomly or at a predetermined interval.

5. The system of claim 1, wherein the remote monitoring system further comprises a pressure sensor located at the exposed surface of the valve plate and configured to measure a pressure of the water and provide an electrical signal representative of the measured pressure to the communication interface.

6. The system of claim 5, wherein the communication interface is configured to transmit pressure information based on the received electrical signal from the pressure sensor to the monitoring system, wherein the monitoring system is configured to determine a leak based on the pressure information.

7. The system of claim 5, wherein the remote monitoring system further comprises a temperature sensor located at the exposed surface of the valve plate and configured to measure a temperature of the water and provide an electrical signal representative of the measured temperature to the communication interface.

8. A monitoring system for a water distribution system, the monitoring system comprising:
    a plurality of remote monitoring systems, wherein each remote monitoring system of the plurality of remote monitoring systems is located at a corresponding fire hydrant of a water distribution system, each remote monitoring system comprising:
        at least one acoustic hydrophone positioned in contact with water of the water distribution system, the at least one acoustic hydrophone configured to collect acoustic information; and
        a communication interface coupled to the at least one acoustic hydrophone to receive the collected acoustic information from the at least one acoustic hydrophone; and
    a central monitoring system in communication with the plurality of remote monitoring systems, the central monitoring system configured to receive collected acoustic information transmitted by the communication interface of each remote monitoring system of the plurality of remote monitoring systems, wherein the central monitoring system is configured to analyze the collected acoustic information received from the plurality of remote monitoring systems and determine whether a leak is present in the water distribution system based on the analyzed acoustic information.

9. The monitoring system of claim 8, wherein the collected acoustic information from each acoustic hydrophone is time synchronized using a time sync signal received by each remote monitoring system.

10. The monitoring system of claim 8, wherein the central monitoring system is configured to determine a size of the leak in the water distribution system based on the analyzed acoustic information.

11. The monitoring system of claim 8, wherein the central monitoring system is configured to determine a location of the leak in the water distribution system based on the analyzed acoustic information.

12. The monitoring system of claim 11, wherein the location of the leak is provided relative to a location of a fire hydrant.

13. The monitoring system of claim 8, wherein each remote monitoring system further comprises a pressure sensor positioned in contact with water of the water distribution system, the pressure sensor configured to collect water pressure information and provide the collected water pressure information to the communication interface.

14. The monitoring system of claim 13, wherein the central monitoring system is configured to receive collected water pressure information transmitted by each remote monitoring system of the plurality of remote monitoring system, wherein the central monitoring system is configured to analyze the collected water pressure information received from the plurality of remote monitoring systems and determine if a leak is present in the water distribution system based on the analyzed water pressure information.

15. The monitoring system of claim 13, wherein each remote monitoring system further comprises a temperature sensor positioned in contact with water of the water distribution system, the temperature sensor configured to collect water temperature information.

16. A method for detecting leaks in a water distribution system, the method comprising:
    collecting acoustic information from a plurality of acoustic hydrophones, each acoustic hydrophone of the plurality of acoustic hydrophones positioned in contact with water of a water distribution system and associated with a fire hydrant of the water distribution system;
    transmitting the collected acoustic information from each acoustic hydrophone of the plurality of acoustic hydrophones to a central monitoring system;
    analyzing, by the central monitoring system, the collected acoustic information transmitted by each acoustic hydrophone; and
    determining whether a leak is present in the water distribution system based on the analyzed acoustic information.

17. The method of claim 16, further comprising time synchronizing the collected acoustic information from each acoustic hydrophone with a time sync signal received by the fire hydrant.

18. The method of claim 16, wherein the collecting acoustic information from a plurality of acoustic hydrophones occurs one of intermittently or continuously.

19. The method of claim 16, further comprising determining a location of the leak in the water distribution system based on the analyzed acoustic information.

20. The method of claim 16, further comprising:
    collecting water pressure information from a plurality of pressure sensors, each pressure sensor of the plurality of pressure sensors positioned in contact with water of the water distribution system and associated with a fire hydrant of the water distribution system;
    transmitting the collected water pressure information from each pressure sensor of the plurality of pressure sensors to the central monitoring system;
    analyzing, by the central monitoring system, the collected water pressure information received from the plurality of pressure sensors; and
    determining whether a leak is present in the water distribution system based on the analyzed water pressure information.

\* \* \* \* \*